US006689106B2

(12) United States Patent
Bush, Jr. et al.

(10) Patent No.: US 6,689,106 B2
(45) Date of Patent: Feb. 10, 2004

(54) RETRACTING NEEDLE ASSEMBLY FOR A SYRINGE

(75) Inventors: Charles L. Bush, Jr., Fairfield, NJ (US); Roger Hoeck, Holdrege, NE (US); Amir A. Sharifi-Mehr, Bloomingdale, NJ (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/353,392

(22) Filed: Jan. 29, 2003

(65) Prior Publication Data

US 2003/0163091 A1 Aug. 28, 2003

Related U.S. Application Data

(63) Continuation-in-part of application No. 10/183,080, filed on Jun. 27, 2002, which is a continuation-in-part of application No. 09/629,566, filed on Jul. 31, 2000, now Pat. No. 6,432,087.

(51) Int. Cl.[7] ............................................. A61M 5/00
(52) U.S. Cl. ...................... 604/181; 604/110; 604/192
(58) Field of Search ................................ 604/110, 192, 604/194, 195, 198, 181

(56) References Cited

U.S. PATENT DOCUMENTS 5,540,660 A * 7/1996 Jenson ........................ 604/110
6,361,524 B1 * 3/2002 Odell et al. ................. 604/187

* cited by examiner

Primary Examiner—Thomas Denion
Assistant Examiner—Jaime Corrigan
(74) Attorney, Agent, or Firm—Jeanne P. Lukasavage; John L. Voellmicke

(57) ABSTRACT

A retracting needle assembly for use with a syringe barrel having a distally-facing annular sealing surface includes an outer hub having a conduit therethrough, a proximally facing annular sealing surface and means for connecting the outer hub to the syringe barrel. An inner hub having a passageway therethrough is provided. The inner hub includes a distally extending stem and a proximal flange for releasably engaging the outer hub. A needle having a sharp distal end and a proximal end is mounted in the passageway of the inner hub so that the sharp distal end projects distally outwardly. An elongate spring is disposed about the stem of the inner hub and is deflected to provide a bias between the inner hub and the outer hub. A hollow sleeve sized to fit within the conduit of the outer hub over the spring is provided. The sleeve has a sharp edge at its distal end for cutting through the flange to activate the retracting needle feature.

23 Claims, 23 Drawing Sheets

RETRACTING NEEDLE ASSEMBLY FOR A SYRINGE

This application is a continuation-in-part of U.S. patent application Ser. No. 10/183,080 filed Jun. 27, 2002 which is a continuation-in-part of U.S. patent application Ser. No. 09/629,566 and filed Jul. 31, 2000 now U.S. Pat No. 6,432,087.

FIELD OF INVENTION

The present invention is generally related to hypodermic syringes and more particularly to syringes that include a needle that is retractable after the intended use to substantially prevent inadvertent exposure to the needle and reuse of the syringe.

BACKGROUND

Hypodermic syringes are widely used in the medical arts for administering medicaments and for drawing body fluid samples. Generally, hypodermic syringes have a metal needle attached either fixedly or removably that has a sharpened distal point for penetrating vial stoppers or patient's skin. The hypodermic syringes and needles have been used for many years with few problems reported when the vast numbers and needles being used are considered. More recently, with the recognition of viral diseases that are transmitted by body fluids and greater sensitivity of the need to protect health care workers from inadvertent contact with previously used needles (commonly referred to as "sharps") as well as the need to reduce criminal misuse of improperly disposed of needles and syringes, syringes and needles that include provisions to prevent reuse have been developed.

Provisions intended to prevent reuse of needles and syringes include a variety of sharps collector systems that are widely used in health care facilities. Other developments include needle attachments that may be readily broken off by practitioners once the syringe has completed its intended use. A variety of shielding mechanisms has been developed; some of which are currently commercially available. While many of these developments have reduced the incidence of inadvertent exposure of healthcare workers to sharps, most of these devices can readily be overcome by an individual determined to obtain and misuse a hypodermic syringe and needle. As a result of this problem, further developments in the art of hypodermic syringes have resulted in syringes with needles that withdraw into the body of the syringe once their intended use is completed.

U.S. Pat. No. 4,838,869 discloses a retractable hypodermic needle configured for one time use wherein the needle is spring loaded and automatically irretrievably retracted into the hypodermic syringe when the syringe plunger is fully depressed, whereby protrusions on the end of the plunger engage tabs holding the spring loaded needle to release the needle for retraction. A potential problem with the design disclosed in this patent is that many times a practitioner may draw and expel a fluid several times during preparation for administration of a medicament, with this design, the practitioner could inadvertently discharge the retraction mechanism. Further, the design would be very difficult to manufacture in large volumes.

U.S. Pat. No. 4,900,307 discloses a hypodermic needle with an enlarged hub that provides provisions for selectively withdrawing the needle into the hub once the syringe and needle have completed their intended usage. While this disclosed design does substantially eliminate the problem of premature discharge of the retraction mechanism, the enlarged hub has a considerable "dead volume" that would result in a significant undeliverable retention of the medicament. Additionally, although the needle is secured in the hub after discharge, the syringe itself is still fully functional after the hub with the needle inside is removed.

U.S. Pat. No. 4,994,034 discloses a hypodermic injection system with a retractable needle wherein the needle retracts within the interior cavity of a syringe plunger. The disclosed invention includes a cylindrical spring housing with resilient fingers which capture a coiled spring that biasly holds a needle holder against the retaining force of the resilient fingers. The plunger in this disclosure has a frangible end, which when engaging the resilient fingers under a predetermined amount of force, dissociate which remaining inwardly-tapered shoulders spread the resilient fingers, allowing the coiled spring to eject the needle and its holder into the interior cavity of the syringe plunger. A syringe manufactured using this disclosure would be complex and difficult to assemble. It is believed that no successful commercial product has been produced using this disclosure.

U.S. Pat. No. 5,019,044 discloses a safety hypodermic syringe with a hypodermic needle fixed connected to a holder plate and constantly supported by a spring for making axial movement. The holder plate is normally retained by a clamp at a ready position for injection. When the plunger of the syringe is pushed to the bottom of the barrel, the needle is released from the clamp and is pushed by the spring to drop and further follow a rubber plug to be squeezed into a chamber in the plunger. Again, no successful commercial product has resulted from this disclosure, which would be complex to manufacture and appears to have a considerable undeliverable dead volume.

Another example of a syringe with a retractable needle is disclosed in U.S. Pat. No. 5,053,010. The disclosed syringe retracts the needle into a hollow plunger additional pressure on the plunger after the contents of the syringe are expelled. The disclosed design incorporates a sliding elastomeric seal which displaces from its forward position to a retracted position, thereby allowing additional forward travel of the plunger to actuate the retraction mechanism. A problem reported with this design is that, because of the soft nature of the seal, the seal may be prematurely displaced during its use in an injection. Attempts to overcome this difficulty by increasing the stiffness of the sealing member could impair the seal integrity.

U.S. Pat. No. 5,180,369 discloses a self-destructive syringe assembly having a needle cannula fixed to a slidable piston. The slidable piston and slidable piston flange are held within the barrel of the syringe assembly by a compressed spring, a guide tube and a shatter ring. The plunger of the syringe assembly is a hollow elongated tube with a thumb flat at one end, a sliding gasket, a plunger shatter plate and a hook rim at the other end. The patent reports that when medicament is injected, the elongated hollow plunger is further thrust into the shatter ring, the shatter ring shatters, further allowing the slidable piston and slidable piston flange to thrust into the plunger shatter plate to shatter. The shattering of the plunger shatter plate causes the slidable piston and needle cannula to be thrust into the hollow plunger by the spring and is thus prevented from re-entering the guide tube. Again, no successful commercial product has resulted from this disclosure.

U.S. Pat. No. 5,180,370 discloses a syringe which has an internal mechanism for retracting the needle into the syringe after the injection has been given. In one disclosed embodiment, the needle is manually retracted by pulling back on the plunger, and in another, the needle is propelled by a compressed spring into a hollow chamber within the plunger. A syringe produced with this disclosure would be complex to manufacture, and no successful commercial product has resulted from this disclosure.

U.S. Pat. 5,188,599 discloses a hypodermic injection system with a needle that retracts within an interior cavity of the syringe plunger. The needle when retracted is held within the plunger. The disclosed device includes a cylindrical spring housing that has resilient fingers which capture a spring under bias holding a needle holder against the retaining force of resilient fingers. The plunger has a frangible end which dissociates when the outwardly tapered shoulders spread the resilient fingers, allowing the coiled spring to eject the needle and its holder into the interior cavity of the syringe plunger. The patent also discloses a body fluid sampling device that includes a double-ended needle for communication with an evacuated blood collection tube. This patent also includes a review of several earlier disclosures related to retractable needles. Attempts have been made to produce commercial products based on the disclosures of this patent, but as yet there is no successful commercial product.

U.S. Pat. No. 5,201,710 discloses a syringe fitted with a clamping device for the needle and with a mechanism to enable the needle to be automatically retractable into the syringe body at the end of an injection. The disclosed device includes inner and outer cylinders, openings at the ends of the outer cylinder, a third opening at an end of the inner cylinder and a closure for the third opening. The disclosed device further includes a needle with a head, a seal, a first spring to push the needle against the closure and a clamping device loaded by a second spring to maintain outward to the syringe and to release the needle. There is a diaphragm in the closure that bends before breaking and a sharp element to break the diaphragm. There also is a closure to prevent the needle from being accessible and a stop to prevent the second cylinder from being moved outwardly after the syringe is used. As is apparent from the description, the device disclosed by this patent is complex and would be difficult to assemble. No successful commercial product has resulted from the disclosure in this patent.

U.S. Pat. No. 5,385,551 discloses a non-reusable medical device that has a needle which is retractable by depression a plunger slidably mounted in the device. The disclosed device includes a front-mounted retraction mechanism that has a needle holder connected to the needle. The needle holder is supported along the axis of the device by a frictionally engaged retainer ring member coupled to the needle holder along an axially aligned sliding interface. The needle holder and retainer are positioned in the front portion of a hollow body. The front of a movable member or plunger presses against the retainer member passing around the needle holder which cannot move forward, thereby separating the retainer from the needle holder. The separation occurs by gradually reducing the extent of the sliding interface area until the retainer member pops loose from the needle holder whereupon the needle holder and needle are retracted into a cavity in the plunger in response to a retraction force applied to the needle holder by a previously compressed spring. Again, the device disclosed in this patent is complex, difficult to manufacture and appears to have significant undeliverable dead volume. Attempts have been made to commercialize products from this disclosure with only limited success.

U.S. Pat. No. 5,407,436 discloses a hypodermic syringe that has a hollow needle that is automatically retractable after use. The disclosed syringe includes a one-piece body molding has a main chamber for a plunger, sample container or drug cartridge, a forward chamber to house a spring to bias a needle holder, and internal latching formations to retain the needle holder with the spring compressed in the forward chamber until automatic retraction when the latching formations are released by end of plunger movement. The patent discloses that the sealing between the plunger and the body is accomplished by an over-sized plunger head that forces head and wall deformation. The disclosed spring has seals at both ends for the forward chamber. The patent teaches that the needle, its holder, spring and seals can be installed using a sliding guide. In using a syringe produced using this disclosure, the practitioner would need to exercise care when drawing and expelling a fluid during filling, because the retraction of the needle is activated by depressing the plunger sufficiently to engage cooperating latches. The engagement occurs at the bottom of the stroke to expel fluid from the syringe.

U.S. Pat. No. 5,769,822 discloses a non-reusable syringe with a hollow plunger that has a seal member thereon. The position of the plunger and the seal relative to the barrel permits the plunger, with sufficient strength, to carry applied pressure through the device during injection of a fluid and yet permit the seal disposed at one end of the plunger to have maximum sealing integrity between the plunger and a cylindrical barrel disposed around the exterior of the plunger to abate leakage of the liquid in a chamber within the barrel, as the plunger is manipulated from an expanded position to and expended position and thereafter to a third or collapsed position.

U.S. Pat. No. 6,010,486 discloses a retracting needle syringe that substantially prevents reuse of the syringe by destroying the plunger rod and the needle hub and additionally, retracts the needle into the plunger rod. The disclosed syringe includes provisions that upon fully depressing the plunger rod and applying distally directed axial force, a frangible portion of the inner hub is broken and the plunger tip dislodges to allow a spring to urge a cutter to open the chamber inside the plunger.

Most of the devices discussed in the above referenced disclosures are somewhat complex, and many require manufacture and assembly of parts with potentially difficult assembly or tight tolerance requirements. Many of the designs depend upon a careful application of forces by the practitioner to draw and expel fluids from the syringe. Also, if the tolerances between the multiple components of the device are not carefully adhered to during manufacture and assembly, normal usage may result in premature activation of the retraction function of the syringe. Current conventional syringes are considered by users to be virtually fault-free and reliable. They are used for a variety of different procedures involving both "one-shot" fill and inject procedures, as well as more complex mixing, measuring and delivery functions. In order for a retractable syringe to displace these functional, utilitarian and reliable conventional syringes, the retractable syringe should not significantly interfere with the users current practices, it needs to be substantially reliable and its cost should not be prohibitive. Current conventional syringes are often manufactured at rates of several hundred per minute and their cost is generally not a significant factor in their usage. Additionally every year, hundreds of millions of small capacity (one milliliter) syringes are used outside of the normal controlled health care environment by diabetics and other self-injectors who must daily accurately inject small amounts, often only a few tenths of a milliliter. These small capacity syringes are physically quite small, with an overall length of less than five inches and an inside bore diameter of less than one-quarter inch. Reviewing the disclosures above, one skilled in the art of high volume manufacturing recognizes that assembling hundreds of millions of most of these relatively complex devices with their retraction elements contained in such a small space as a one-quarter inch diameter bore is a daunting task. Additionally, many of the disclosed devices have substantial undeliverable "dead volumes" that substantially confound many diabetics' need for accurate measuring, mixing of more than one type of insulin in the syringe and delivering small doses of insulin. The need thus exists for a selectively retractable syringe that is compatible with a small capacity syringe, that is capable of being manufactured at high volumes and is sufficiently non-complex to be reliable in use when produced at volumes of hundreds of millions per year. Such a device is disclosed herein below.

SUMMARY

A hypodermic syringe with a selectively retractable needle of the present invention includes an elongate barrel having an open proximal end and a distal end that defines a receiver with an inwardly projecting shoulder. The barrel has a hollow bore therethrough with an inside surface extending from the proximal end to the distal end. The syringe of the invention has a hollow elongate plunger with an open proximal end and a closed distal end. There is an elongate plug extending distally into the hollow plunger from the open proximal end forming an enclosed cavity within the plunger. The distal end of the plunger forms a slidable seal with the inside surface of the barrel to define a chamber for drawing and expelling fluid. The syringe also has an elongate hub having a passageway therethrough, a distally extending stem, and a proximal flange with an engagement for engaging the barrel. The stem is disposed within and sized for slidable movement within the receiver at the distal end of the barrel. The flange has a distal surface with a groove therein and a proximal surface defining the chamber in the barrel. The syringe of the invention has an elongate needle having a fluid path therethrough, a sharpened distal end and a proximal end. The needle is mounted in the passageway in the hub so that the sharpened distal end projects distally outwardly and the fluid path is fluidly communicative with the chamber in the barrel. The syringe also has an elongate spring disposed about the stem of the hub that is compressed between the flange and the inwardly projecting shoulder of the receiver to provide a bias. There is a hollow sleeve sized to fit within the receiver over the elongate spring. The sleeve has a distal end disposed at shoulder and a proximal end with a sharpened edge that is disposed in the groove in the distal surface of the flange. When a user applies a sufficient force, a force greater than necessary to expel fluid from the chamber, to the plunger, the hub is sufficiently moved distally in the receiver for the cutting edge of the sleeve to cut through the flange and the closed distal end of the plunger to expose the cavity in the plunger. When the cavity in the plunger is exposed, the bias of the spring urges a sufficient movement of a cut portion of the hub having the needle mounted therein, a cut portion of the distal end of the plunger and the sleeve into the cavity in the plunger to a position wherein an inadvertent exposure of the sharpened distal point is substantially prevented.

The syringe of the invention has an undeliverable "dead-space" volume substantially similar to fixed needle "low dead-space" conventional syringes, i.e., substantially no undeliverable volume. The syringe of the invention is as suitable for use in drawing, measuring, mixing and delivering small volumes of medicaments as conventional syringes. Unlike many of the devices disclosed above, the syringe of the invention is substantially unlikely to be inadvertently retracted by a user following currently used practices and procedures. The syringe of the invention does not depend on a user having to exercise substantially more care than with a conventional syringe when drawing and mixing fluids in the syringe to avoid inadvertent activation, and importantly, the syringe of the invention is compatible with the efficiency of high volume automated manufacture that utilizes much existing manufacturing equipment. Once needle is retracted in the syringe of the invention, the syringe cannot be restored to functionality, as the hub flange is cut through and the plunger is cut through rendering the syringe substantially unusable and protecting the needle point from inadvertent contact by anyone.

An alternate embodiment of the syringe of the present invention includes an elongate barrel having an open proximal end and a distal end defining a receiver. The barrel also includes a hollow bore therethrough. A hollow elongate plunger having a proximal end and a distal end defining a cavity therein is provided. The distal end of the plunger forms a slidable seal with the inside surface of the barrel. An elongate hub comprises a passageway therethrough including a distally extending stem, and a proximal flange with an engagement for engaging the barrel. The stem being disposed within and sized for movement in the receiver at the distal end of the barrel. The flange of the hub includes a distal surface and a proximal surface. An elongate needle having a fluid path therethrough is connected to the stem of the hub so that the passageway is in fluid communication with the chamber of the barrel. An elongate spring is disposed about the stem of the hub. The spring is compressed to provide a biasing force to the flange. A hollow sleeve sized to fit within the receiver includes a distal end and a proximal end having a cutting edge facing the distal surface of the flange of the hub so that when the user supplies a sufficient force, greater than a force necessary to expel fluid from the chamber, to the plunger, the hub is sufficiently moved distally in the receiver for the cutting edge of the sleeve to cut through the flange and the closed distal end of the plunger to expose the cavity therein. This allows the bias of the spring to urge a sufficient proximal movement of the cut portion of the hub having the needle mounted therein and the cut portion of the distal end of the plunger into the cavity. In the event that the frictional force between the inside of the sleeve and the cut portions of the hub and the plunger is greater than the frictional force between outside of the sleeve and the remaining portions of the hub and the plunger, the spring will move the from its position in the receiver so that the cut portion of the hub, the cut portion of the distal end of the plunger and the sleeve move into the cavity. If the frictional force on the outside of the sleeve is greater than the frictional force on the inside of the sleeve the sleeve will remain in its position in the receiver while the cut portion of the hub and the cut portion of the distal end of the plunger move into the cavity.

An operable retracting needle assembly for use with a syringe barrel assembly includes a syringe barrel having an inside surface defining a chamber, an open proximal end, an open distal end including a needle assembly engaging structure and a distally-facing annular sealing surface. The syringe barrel assembly also includes a hollow elongate plunger having a proximal end and a closed cuttable distal end defining a cavity therein. The distal end of the plunger forming a slidable seal with the inside surface of the barrel.

The retracting needle assembly comprises an outer hub having a proximal end, a distal end and an inside surface defining a conduit therethrough. A proximal-facing annular sealing surface and an inwardly directed shoulder in the conduit are provided. The outer hub includes means for connecting the outer hub to the needle assembly engaging structure of the syringe barrel so that the proximally-facing annular sealing surface contacts the distally-facing annular sealing surface of the syringe barrel. An elongate inner hub includes a passageway therethrough, a distally extending stem, and a proximal flange with an engagement for releasably engaging the conduit of the outer hub. The stem is disposed within and sized for slidable movement within the cavity of the outer hub. The flange includes a distal surface and a proximal surface. A needle having a sharp distal end, a proximal end and a passageway therethrough is provided. The proximal end of the needle is mounted in the passageway of the inner hub so that the sharp distal end projects distally outwardly. An elongate spring is disposed around the stem of the inner hub and is deflected to provide a bias between the flange and the inwardly projecting shoulder. A hollow sleeve is sized to fit and is positioned within the conduit of the outer hub over the spring. The sleeve includes a distal end disposed at the shoulder and a proximal end having a sharp edge facing the distal surface of the flange so that when the needle assembly is installed on the syringe assembly and a distally directed force, greater than the force required to expel fluid from the chamber, is applied to the plunger, the inner hub is moved sufficiently distally in the outer hub for the sharp edge of the sleeve to cut through the flange and the closed distal end of the plunger to expose the cavity therein. This allows the bias of the spring to urge a sufficient proximal movement of a cut portion of the hub having a needle mounted therein and a cut portion of the distal end of the plunger into the cavity in the plunger to a position wherein inadvertent exposure of the sharp distal point is substantially prevented. The needle assembly may also include an elongate hollow needle shield having a distal end, and an open proximal end removably engaged to the needle assembly so that the needle shield covers the needle.

The retracting needle assembly may include engagement structure wherein the inside surface of the conduit of the outer hub has one of a depression therein or a protuberance thereon, and wherein the flange of the inner hub has a conjugate to one of the depression and the protuberance, so that when the stem is disposed in the conduit with the spring compressed between the flange and the shoulder, the conjugates are engaged thereby releasably retaining the inner hub in the outer hub.

The retracting needle assembly may also contain a sleeve having an outward step adjacent to its proximal end. The step serves to accept the cut portion of the flange to reduce resistance to the advancement of the cutter into the distal end of the plunger. The needle assembly may also be sealed in a package formed of material substantially resistant to the passage of microorganisms and further exposed to conditions that render any microorganisms therein substantially non-viable.

DETAILED DESCRIPTION

Figure 1:
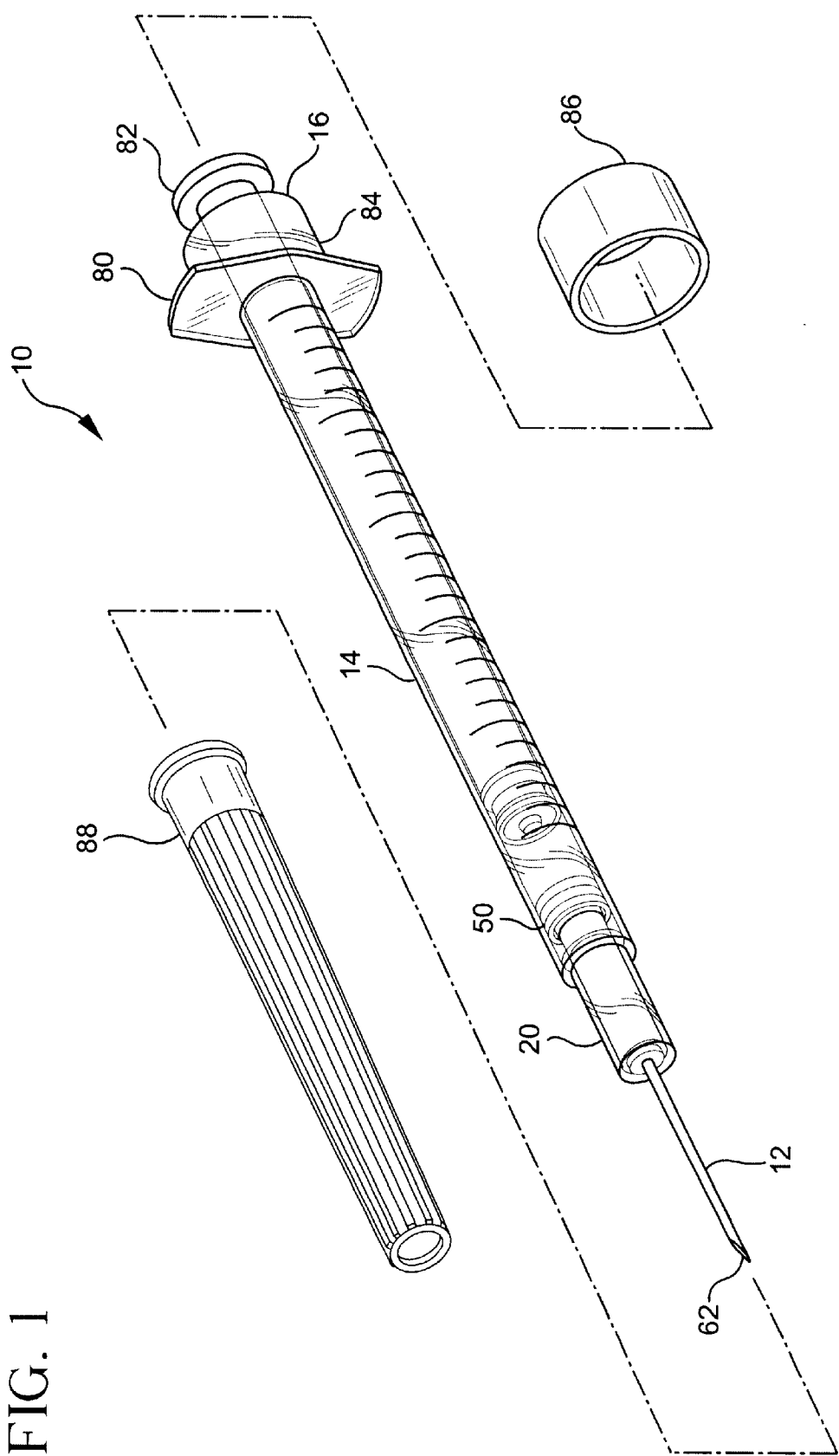
FIG. 1 is a partially exploded perspective view of the hypodermic syringe of the invention.
Figure 2:
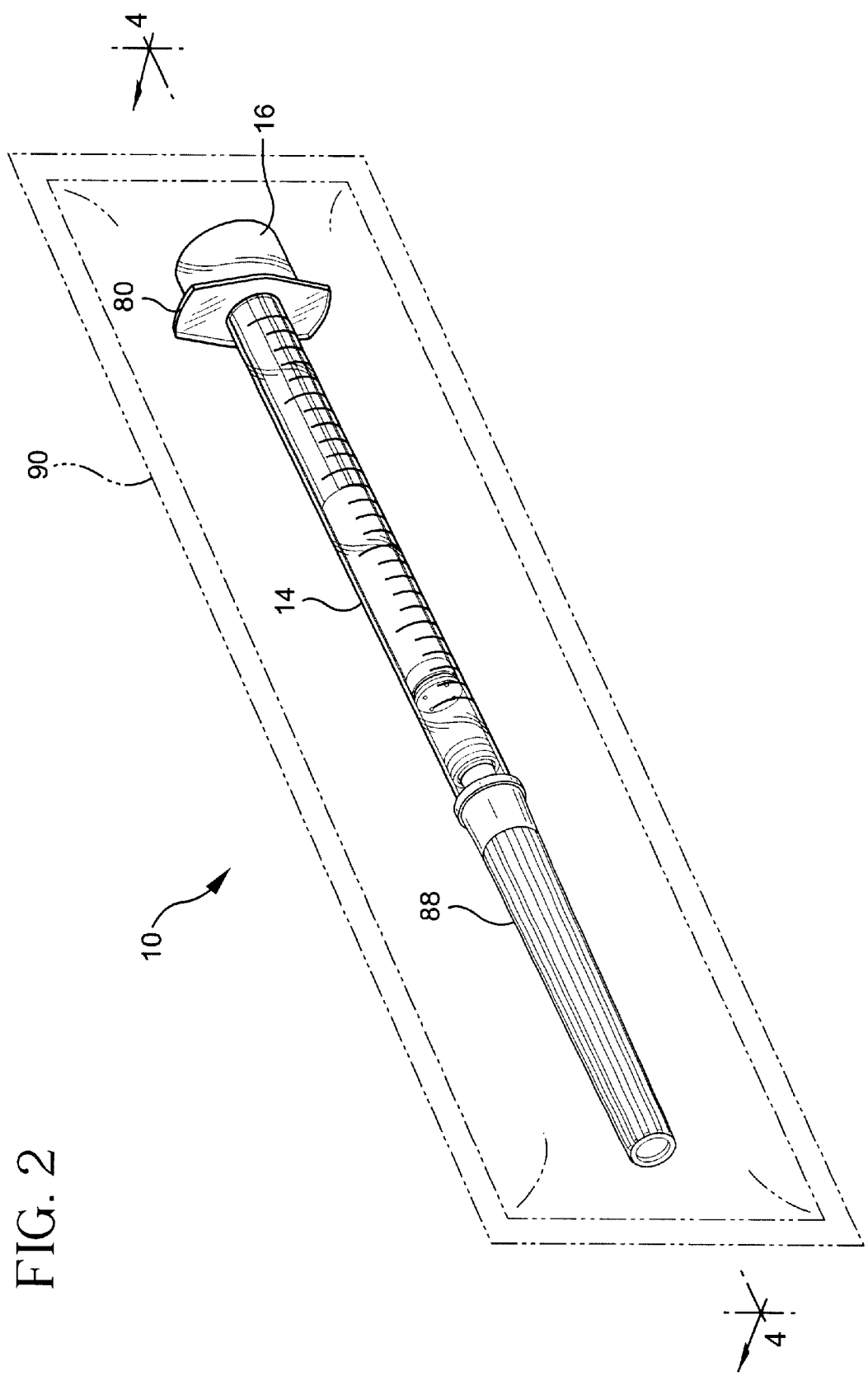
FIG. 2 is a perspective view of the hypodermic syringe of FIG. 1 assembled and sealed in a package.

While this invention is satisfied by embodiments in many different forms, there are shown in the drawings and herein described in detail, embodiments of the invention with the understanding that the present disclosure to be considered as exemplary of the principles of the present invention and is not intended to limit the scope of the invention to the embodiments illustrated. The scope of the invention is measured by the appended claims and the equivalents. In this disclosure, a convention is followed wherein the distal end of the device is the end closest to a patient and the proximal end of the device is the end away from the patient and closest to a practitioner.

Figure 6:
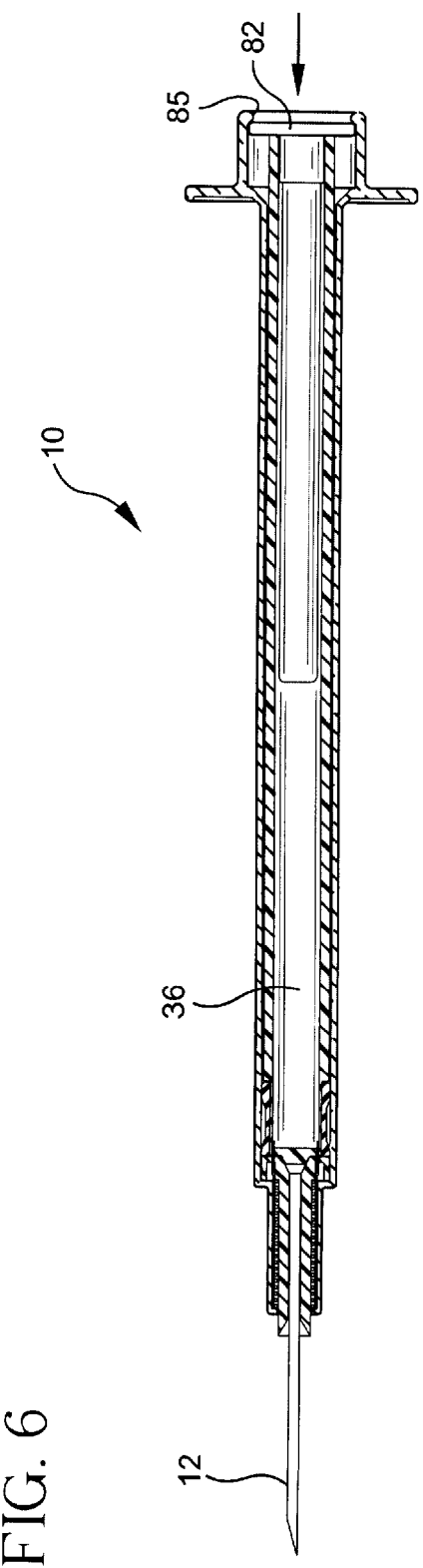
FIG. 6 is a schematic cross-sectional view of the hypodermic syringe of FIG. 1 with the plunger moved distally to activate the needle retraction sequence.
Figure 6A:
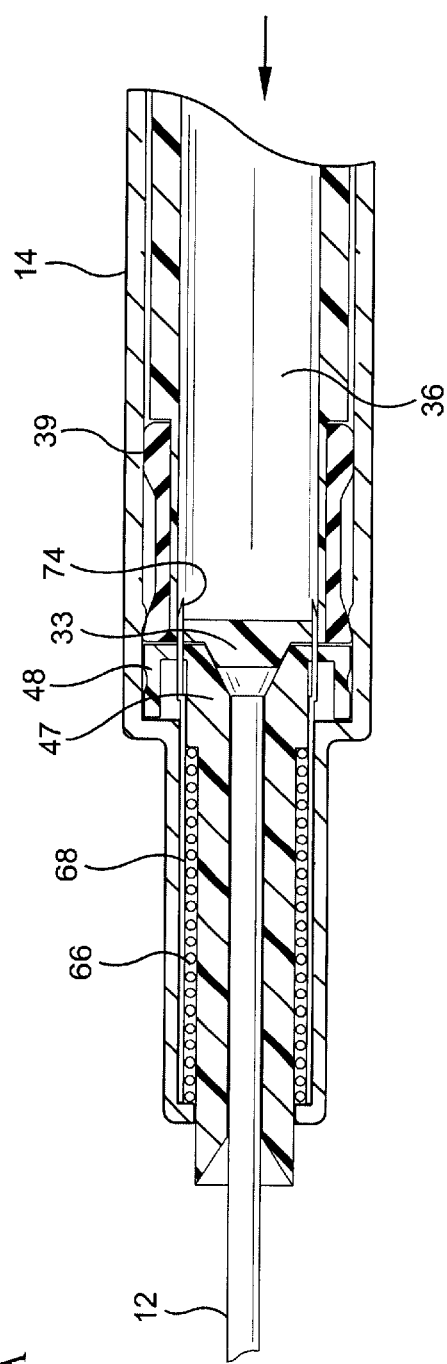
FIG. 6a is an enlargement of the distal portion of the cross-sectional view of FIG. 6.
Figure 7:
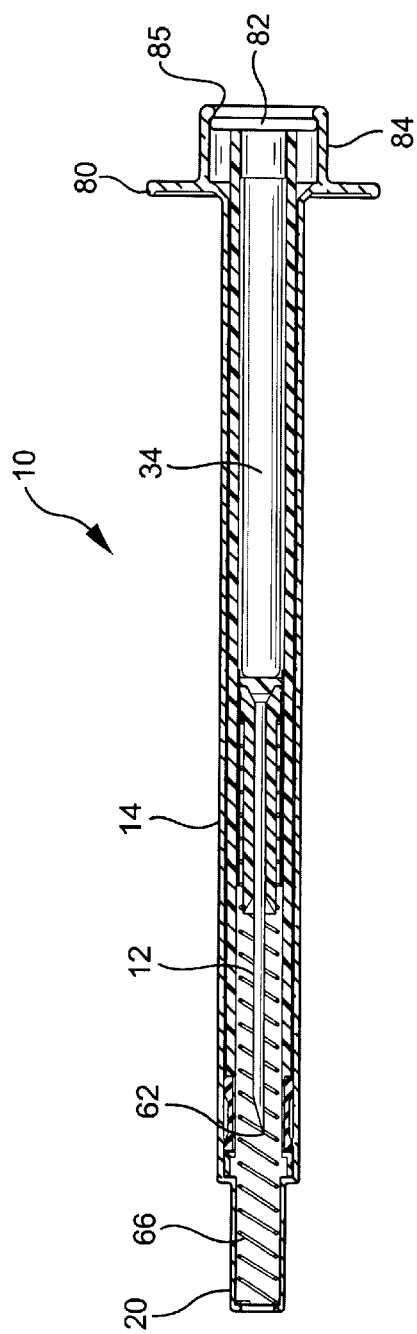
FIG. 7 is a cross-sectional view of the hypodermic syringe of FIG. 1 after the needle retraction sequence is completed.
Figure 7A:
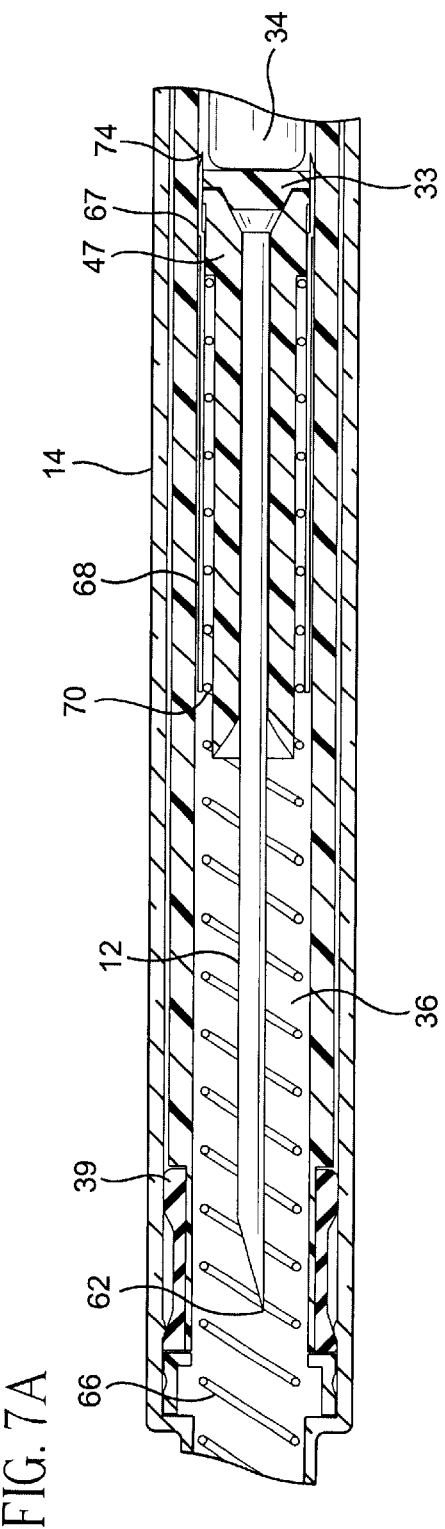
FIG. 7a is an enlargement of a portion of the cross-sectional view of FIG. 7.

Referring to the FIGS. 1–8a, a hypodermic syringe 10 with a selectively retractable needle 12 of the present invention includes an elongate barrel 14 having an open proximal end 16 and a distal end 18 that defines a receiver 20 with an inwardly projecting shoulder 22. Barrel 14 has a hollow bore 24 therethrough with an inside surface 26 extending from proximal end 16 to distal end 18. Syringe 10 has a hollow elongate plunger 28 with an open proximal end 30 and a closed distal end 32. There is an elongate plug 34 extending distally into hollow plunger 28 from open proximal end 30 forming an enclosed cavity 36 within the plunger. Distal end 32 of plunger 28 forms a slidable seal 38 with inside surface 26 of the barrel to define a chamber 40 for drawing and expelling fluid. Syringe 10 also has an elongate hub 42 having a passageway 44 therethrough, a distally extending stem 46, a proximal flange 48 with an engagement 50 for engaging the barrel, stem 46 being disposed within and sized for slidable movement within receiver 20 at distal end 18 of the barrel, flange 48 having a distal surface 52 having a groove 54 therein and a proximal surface 56 defining chamber 40 in the barrel. Syringe 10 of the invention has elongate needle 12 having a fluid path 60 therethrough, a sharpened distal end 62 and a proximal end 64. Needle 12 is mounted in passageway 44 in hub 42 so that sharpened distal end 62 projects distally outwardly and fluid path 60 is fluidly communicative with chamber 40 in the barrel. Syringe 10 also has an elongate spring 66 disposed about stem 46 of hub 42 that is compressed between flange 48 and inwardly projecting shoulder 22 of receiver 20 to provide a bias. There is a hollow sleeve 68 sized to fit within receiver 20 over elongate spring 66. Sleeve 68 has a distal end 70 disposed at shoulder 22 and a proximal end 72 with a sharpened cutting edge 74 that is disposed in groove 54 in distal surface 52 of the flange. When a user applies a sufficient force, as illustrated in FIGS. 6 and 6a, a force greater than necessary to expel fluid from chamber 40, to plunger 28, hub 42 is sufficiently moved distally in receiver 20 for cutting edge 74 of sleeve 68 to cut through flange 48 and closed distal end 32 of the plunger to expose cavity 36 in the plunger as seen in the FIGS. When cavity 36 in the plunger is exposed, the bias of spring 66 urges a sufficient movement of a cut portion 47 of the hub having needle 12 mounted therein, a cut portion 33 of distal end 32 of the plunger and sleeve 68 into cavity 36 in the plunger to a position, best seen in FIGS. 7 and 7a, wherein an inadvertent exposure of sharpened distal point 62 is substantially prevented. Preferably, closed distal end 32 of the plunger includes a projection 35 that is sized and shaped to engage a conjugate taper in flange 48 to hold the flange in position when sharpened end 74 cuts into the flange and the closed distal end of the plunger.

Figure 3:
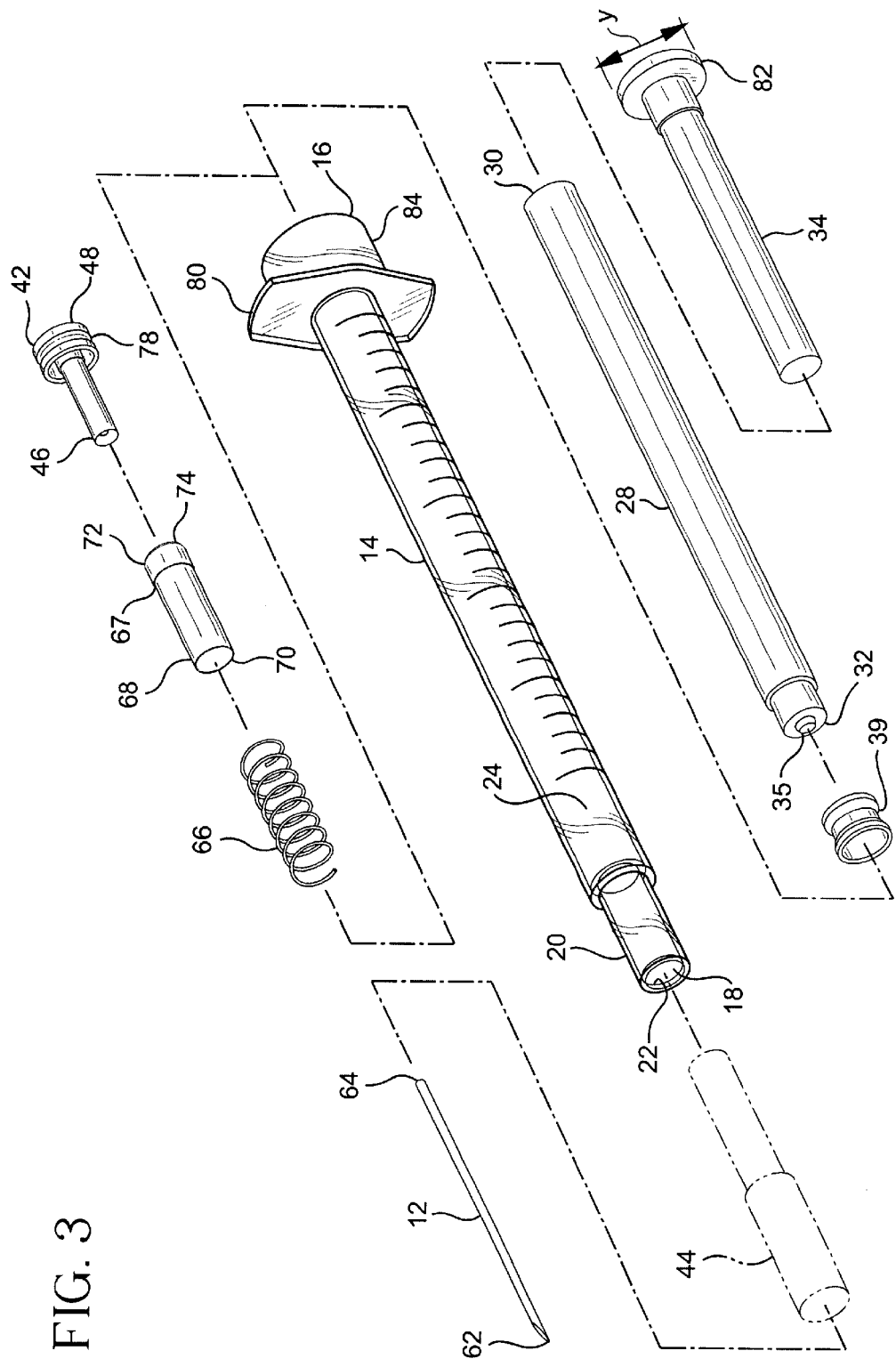
FIG. 3 is an exploded perspective view of the hypodermic syringe of FIG. 1.
Figure 4:
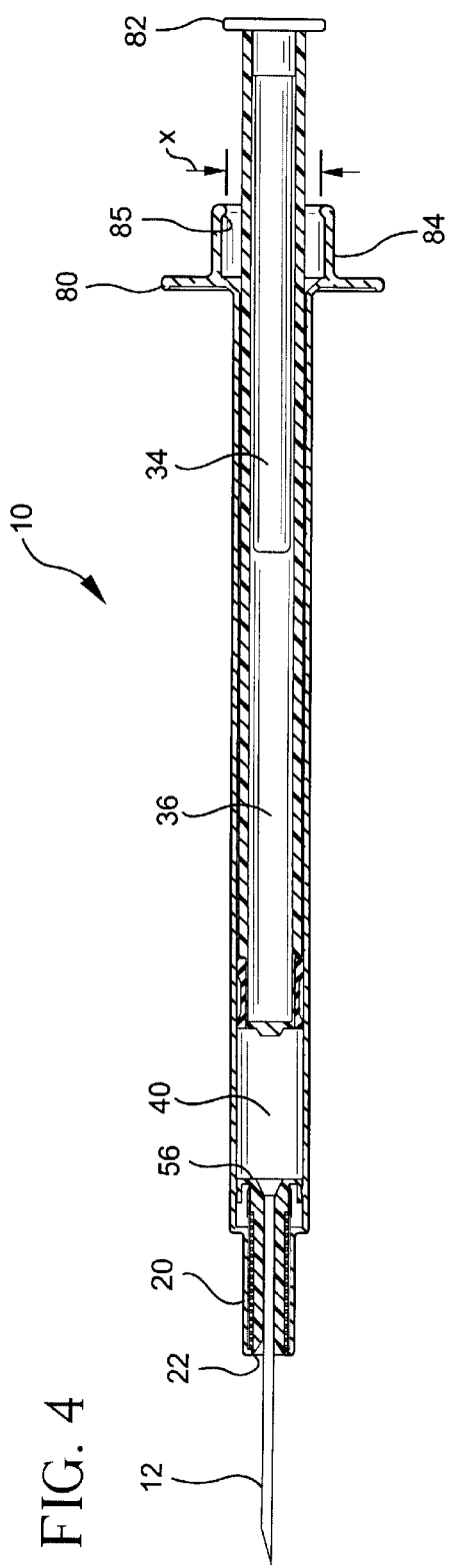
FIG. 4 is a schematic cross-sectional view of the hypodermic syringe of FIG. 1 with the plunger partially distally retracted taken on the line 4—4.

Referring to FIGS. 3 and 4, slidable seal 38 on plunger 28 is preferably formed by a resilient sealing member 39 that substantially surrounds a portion of plunger 28 adjacent distal end 32 leaving the distal end exposed. Sealing member 39 may be formed from resilient materials such as natural rubber, synthetic rubber, thermoplastic elastomer and combinations. Suitable materials include a separate gasket, one or more "O" rings and the like. Preferably, sealing member 39 is formed from a resilient thermoplastic elastomer that is integrally formed with plunger 28 as a single article of manufacture. Plunger 28 is preferably formed by an injection molding process from thermoplastic materials such as polypropylene, polyethylene, polystyrene, polycarbonate, copolymers of theses materials and the like, with the thermoplastic elastomeric material selected for sealing member 39 being selected as a material that may be successfully co-injected with the material selected for the used to form plunger 28 as a single article of manufacture including sealing member 39.

Referring now to FIGS. 3–7a, sleeve 68 preferably includes an outward step 67 adjacent proximal end 72. When the needle retraction process is initiated by the user's application of sufficient distal force to plunger 28, best seen in FIGS. 5–6a, outward step 67 serves as a receptacle for cut portion 47 of flange 48, when sharpened edge 74 cuts through flange 48. As further distal force is applied to plunger 28 by the user, cutting edge 74 cuts through distal end 32 of plunger 28 to expose cavity 36 by cutting portion 33 from distal end 32. Once cavity 36 is exposed, spring 66 urges sleeve 68, with cut portions 33 and 47 into cavity 36 thereby withdrawing needle 12 to a position, best seen in FIGS. 7 and 7a, where sharpened distal end 62 is within syringe 10 and substantially protected from inadvertent contact. By containing cut portions 33 and 47 within the receptacle formed by step 67, the reliability of the retraction is facilitated because the contained cut portions are substantially unable to interfere with the movement of sleeve 68 and needle 12.

Sleeve 68 is preferably formed from a metallic material such as carbon steel, stainless steel and the like. Preferably, sleeve 68 is formed by deep drawing of stainless steel and then subjected to a secondary process such as grinding, honing, polishing, electrochemical processing or combinations of these processes to produce sharpened cutting edge 74 at proximal end 72 of the sleeve. Electrochemical processing after forming is most preferred.

Referring to FIGS. 4–7a, hollow bore inside surface 26 preferably includes a protuberance 76 thereon for interacting with a conjugate depression 78 on flange 48 to form engagement 50 with protuberance 76. Engagement 50 serves to hold hub 42 in position in the barrel so that needle 12 projects outwardly with spring 66 in compression between flange 48 and shoulder 22 of the receiver.

Figure 9:
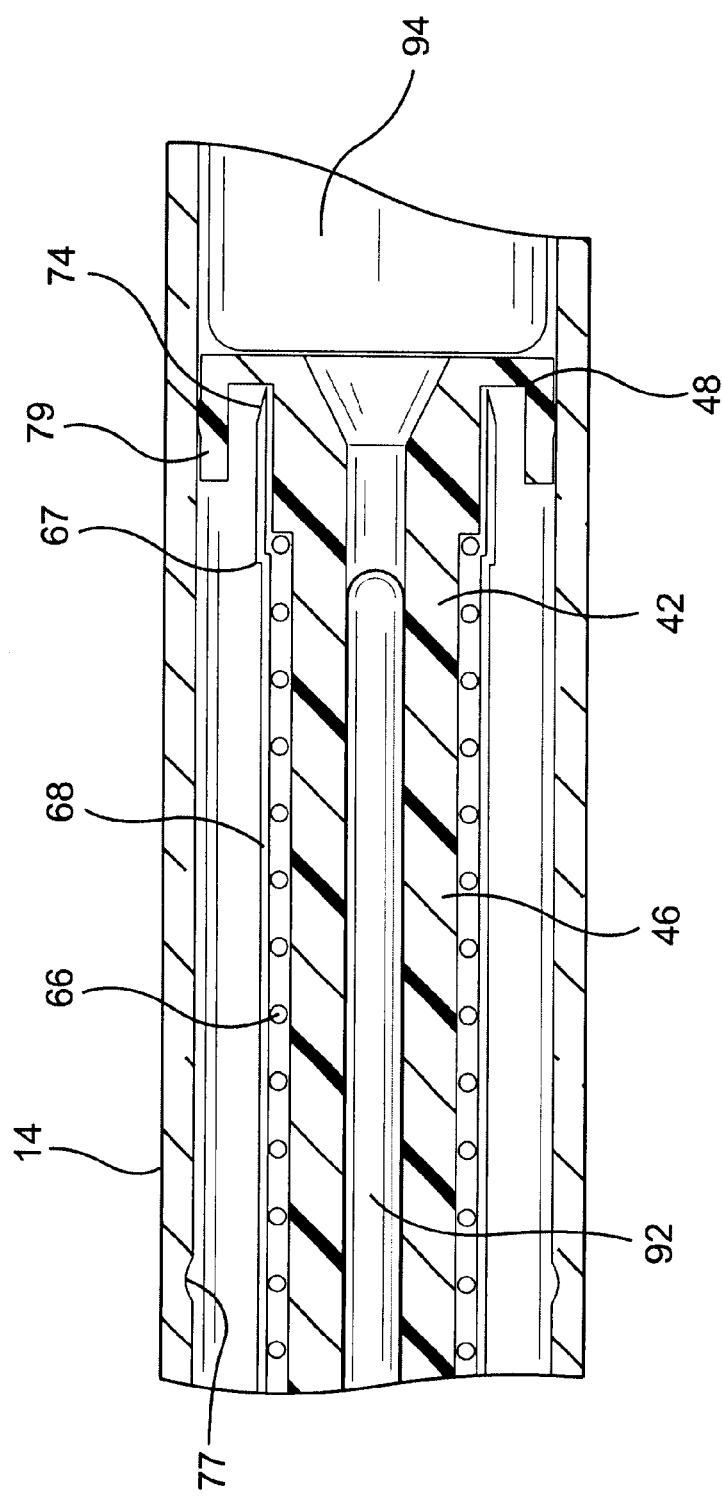
FIG. 9 is an illustration of an alternate embodiment of a portion of the hypodermic syringe of FIG. 1.

Referring now to FIG. 9, an alternate preferred embodiment to the engagement 50 is illustrated. In this embodiment, hollow bore inside surface includes a depression 77 to engage a conjugate protuberance 79 on flange 48. In this alternate embodiment, the conjugates 77 and 79 again engage to retain hub 42 in position within the barrel.

Figure 4A:
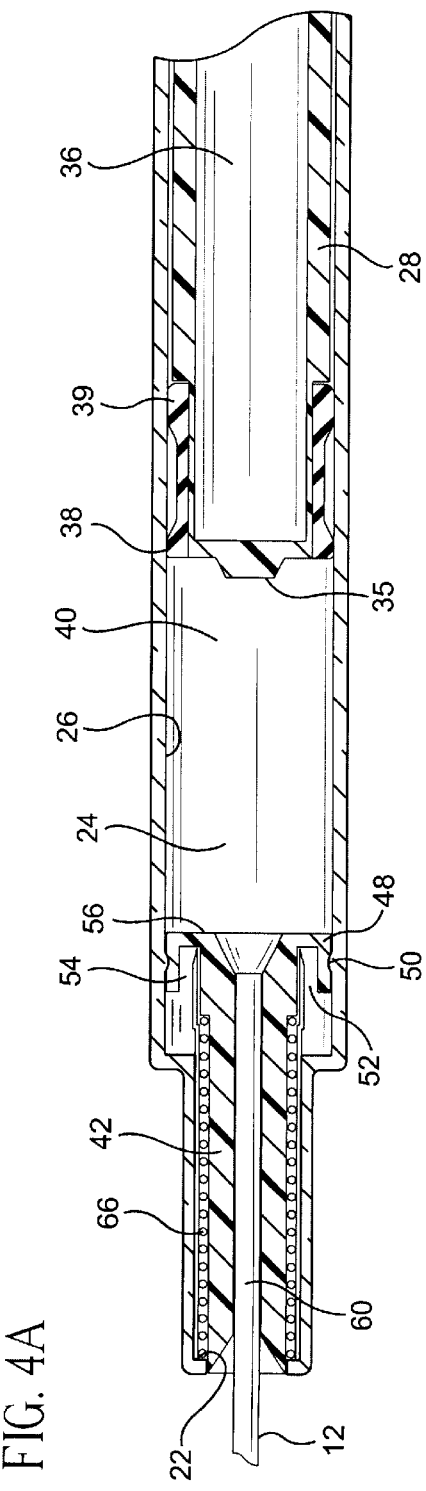
FIG. 4a is an enlargement of a distal portion of the cross-sectional view of FIG. 4.
Figure 5:
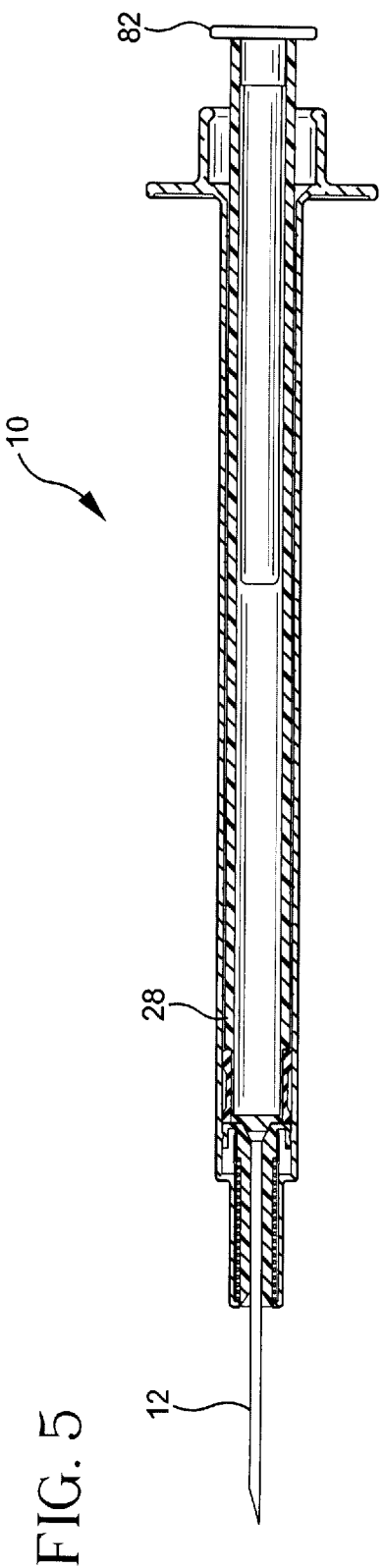
FIG. 5 is a schematic cross-sectional view of the hypodermic syringe of FIG. 1 with the plunger at the distal end of the barrel taken on the line 5—5.
Figure 5A:
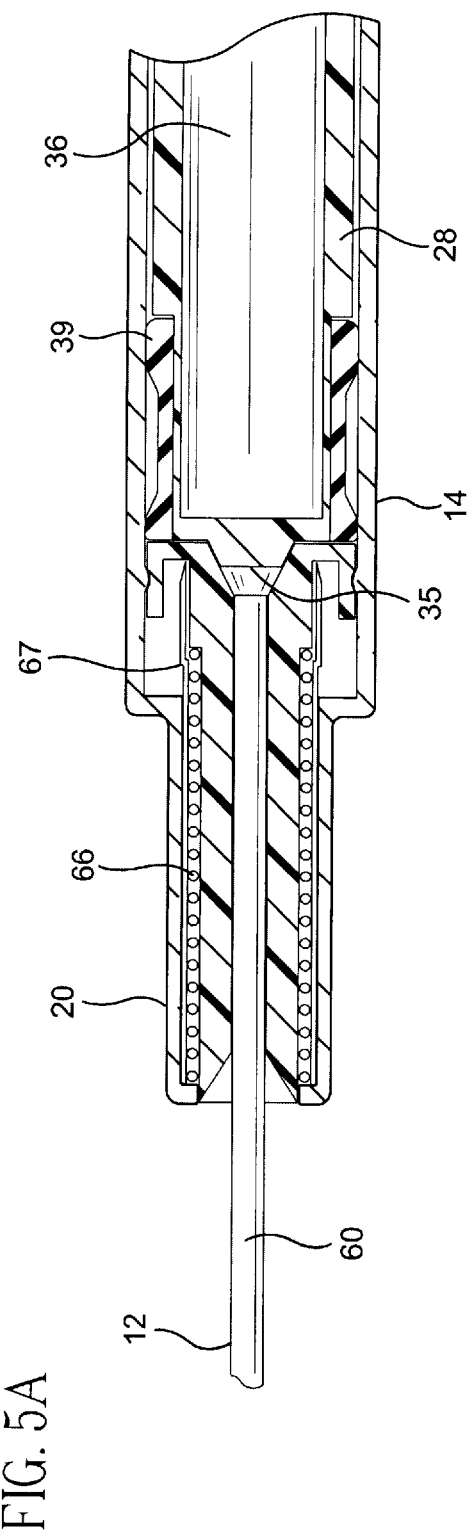
FIG. 5a is an enlargement of the distal portion of the cross-sectional view of FIG. 5.

Returning to FIGS. 3 and 4a, proximal end 16 of barrel 14 further includes a finger grip 80 to facilitate a users grip of the syringe. Additionally, elongate plug 34 is preferably retained in open plunger 28 by an interference fit and includes a finger press 82 with an outside diameter "y". Finger press 82 is disposed at proximal end 30 of plunger 28 to facilitate the user's movement of plunger 28 to draw and expel fluid from chamber 40 and to apply additional force to the plunger to initiate the retraction of needle 12. Finger grip 80 also includes a collar 84 that preferably has an inner projection 85 with an inside diameter "x" that is less than outside diameter "y" of the finger press. When the force greater than the force required to expel fluid from chamber 40 is applied so that needle 12 is retracted into the syringe barrel, finger press 82 is moved distally past the interference between diameters "x" and "y", substantially contained within collar 84 and thereby substantially retained in the collar by projection 85. At this point, flange 48 is cut through, plunger distal end 32 is cut through, spring 66 has urged the movement of needle 12 into the syringe and finger press 82 is substantially retained in collar 84 thus rendering syringe 10 substantially non-reusable.

Figure 11:
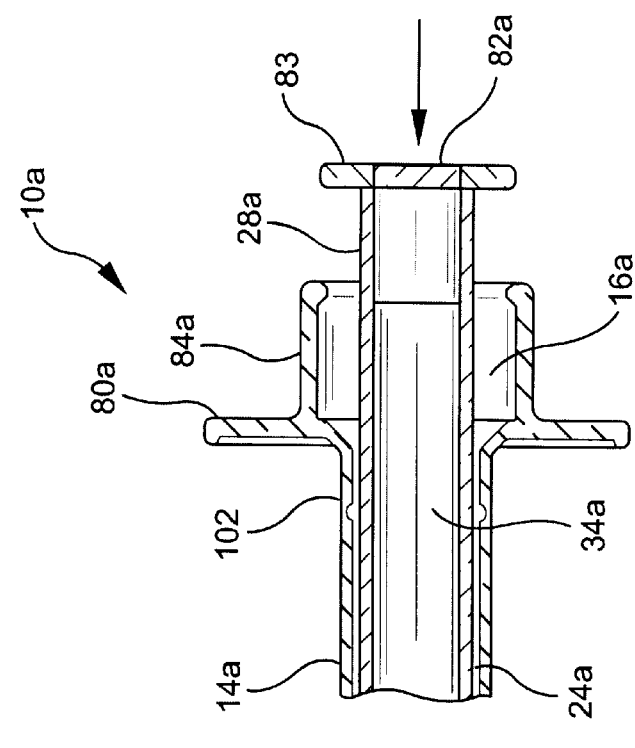
FIG. 11 is an illustration of the embodiment of FIG. 10 in a portion of a cross-sectional view, analogous to FIG. 6, of the hypodermic syringe of FIG. 1.
Figure 10:
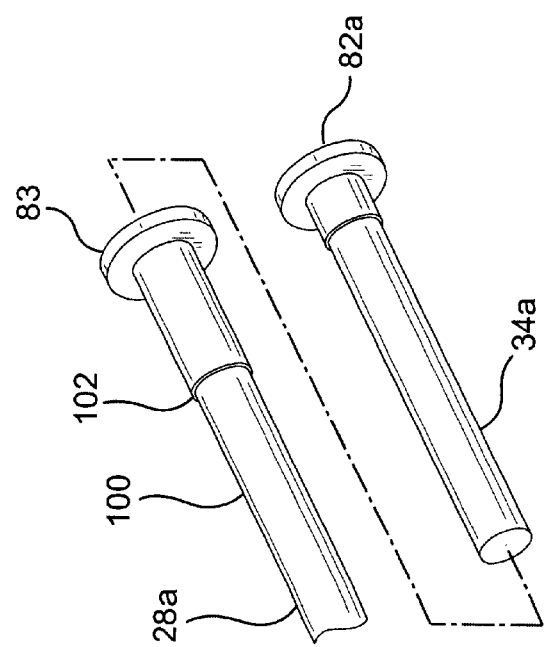
FIG. 10 is an illustration of an alternate embodiment of another portion of the hypodermic syringe of FIG. 1.

Referring to FIGS. 10 and 11, an alternate embodiment of plunger 28 and proximal end 16 is illustrated. In this embodiment which may be preferred for particular applications, components having similar function to those in FIGS. 1–8a are shown with the addition of a suffix a. The Figs. show the proximal portion of plunger 28a, analogous to the proximal portion of plunger 28 in FIG. 3 and a proximal portion of barrel 14a, analogous to that shown in FIG. 6. In this embodiment, plunger 28a has an outside surface 100 that includes a portion 102 having an enlarged diameter disposed proximally. Hollow bore 24a of the barrel has an inside diameter larger than enlarged portion 102 at proximal end 16a than at a distance distally. This enlarged diameter allows plunger 28a freedom to slidably move proximally and distally in the barrel for drawing and expelling fluid from chamber 40. When a sufficient force, greater than the force necessary to expel fluid from chamber 40 is applied to plunger 28a so that the retraction sequence is initiated, as shown in FIGS. 4–6a, enlarged portion 102 engages the inside diameter of hollow bore 24a and substantially prevents further movement of plunger 28a thereby retaining plunger 28a in barrel 14a. In this embodiment, plug 34a includes a thumb press area 82a that fits through an opening in thumb press 83 that is part of plunger 28a to form the thumb press for the plunger. In this embodiment, collar 84a serves only to accept a cap, thumb press area 82a and 83 projects beyond collar 84a to facilitate the user's drawing and expelling fluid from chamber 40 of the barrel.

Referring back to FIGS. 1 and 2, syringe 10 preferably further includes a removable cap 86 sized to engage an exterior surface of collar 84 and cover finger press 82 of the plunger as well as a removable shield 88 sized to engage receiver 22 and cover distally extending needle 12. Syringe 10 also may be sealed in a package 90 formed from materials substantially resistant to the passage of microorganisms and exposed to conditions that render any microorganisms within substantially non viable. Cap 86 and shield 88 preferably are frangibly attached to collar 84 and receiver 20 respectively. When the cap and shield are frangibly attached, and syringe 10 is exposed to conditions that render microorganisms substantially non-viable, a user can be substantially assured that the syringe is unused and that the fluid path of the syringe is substantially free of microorganisms until the frangible attachments are breached and the cap and shield is removed. Suitable frangible attachments include, but are not limited to heat staking, laser welding, paper or film labels, and the like. Sealed package 90 also serves as a tamper-evidence feature. Suitable materials for forming package 90 include, but are not limited to paper, polymeric film, foil, non-wovens and combinations thereof. Suitable conditions for rendering microorganisms non-viable include, but are not limited to ionizing radiation such as gamma, electron beam and ultra-violet, exposure to chemical agents such as ethylene oxide, gaseous peroxide and the like. When selecting materials for forming syringe 10 and package 90, consideration should be given to the sterilization conditions to ensure that the materials selected are compatible with the sterilization method selected.

Figure 8:
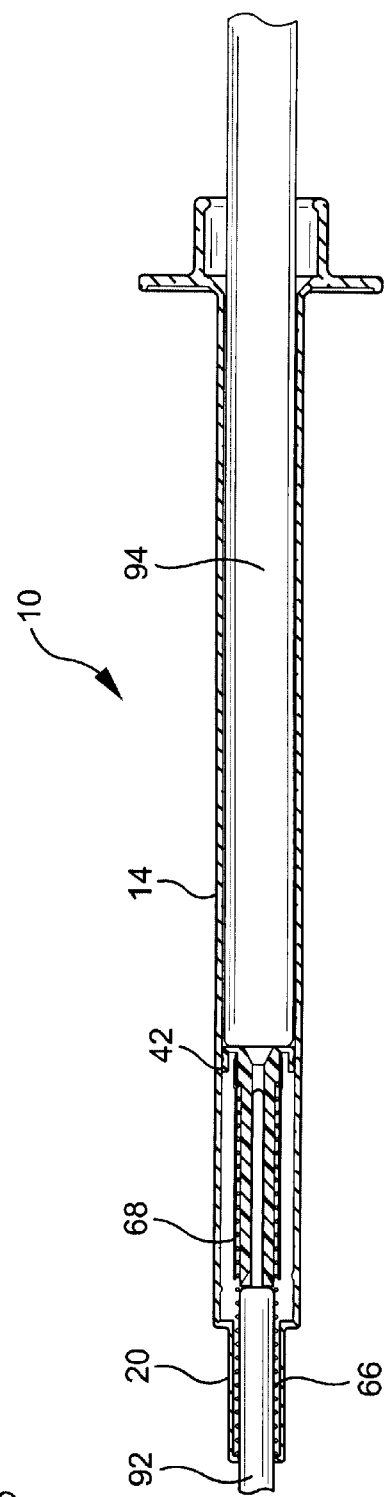
FIG. 8 is a schematic cross-sectional view of a method of assembly of the hypodermic syringe of FIG. 1.
Figure 8A:
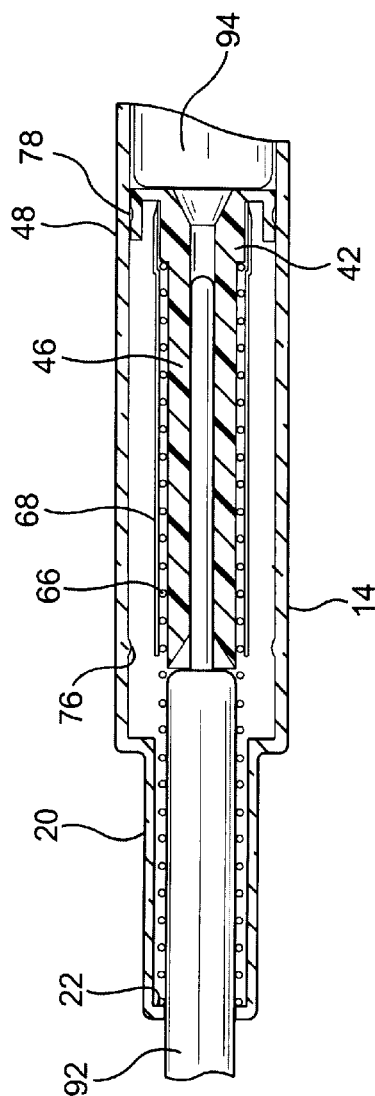
FIG. 8a is an enlargement of the distal portion of the cross-sectional view of FIG. 8.

Referring now to FIGS. 8 and 8a, a method for assembling hypodermic syringe 10 includes inserting an assembly pin 92 into distal end 18 of barrel 14 through hollow bore 24 to a position where pin 92 projects beyond proximal end 16 of the barrel. Hub 42 is then acquired by an assembly mandrel 94, preferably with flange 48 being held by a vacuum against mandrel 94 with stem 46 extending distally and axially aligned with assembly pin 92. Pin 92 is preferably shaped to engage stem 46. Sleeve 68 is placed on assembly pin 92 followed by spring 66 and assembly mandrel 94 is advanced so that stem 46 engages assembly pin 92. Assembly mandrel 94 and assembly pin 92 are then distally advanced through hollow bore 24 until spring 66 is compressed between receiver shoulder 22 and flange 48 with engagement 50 being formed between the conjugate protuberance 76 and depression 78 on flange 48. Once engagement 50 is formed, the assembly pin and the assembly mandrel are withdrawn and barrel 14 is ready for further assembly. Needle 12 is mounted in passageway 44 so that distal point 62 projects outwardly. Plunger 28 is then introduced into proximal end 16 of the barrel and advanced distally to complete the assembly of syringe 10 with selectively retractable needle 12.

Syringe 10 of the invention provides users with a selectively retractable needle syringe that is substantially usable in most normal use techniques. Unlike many of the devices disclosed in the patents referenced above, syringe 10 of the invention is compatible with many current assembly practices and machines, thus is well suited for the high speed, high volume manufacture necessary for commercial success. Additionally, since the retraction mechanism is both simple and positive, syringe 10 may readily be manufactured in small sizes such as a one milliliter capacity with an inside bore diameter of about one quarter inch. The syringe of the invention provides users of conventional small capacity syringes with a selectively retractable alternate that does not appear or function significantly differently from the current devices, thus addressing a need in the medication delivery industry.

Figure 12:
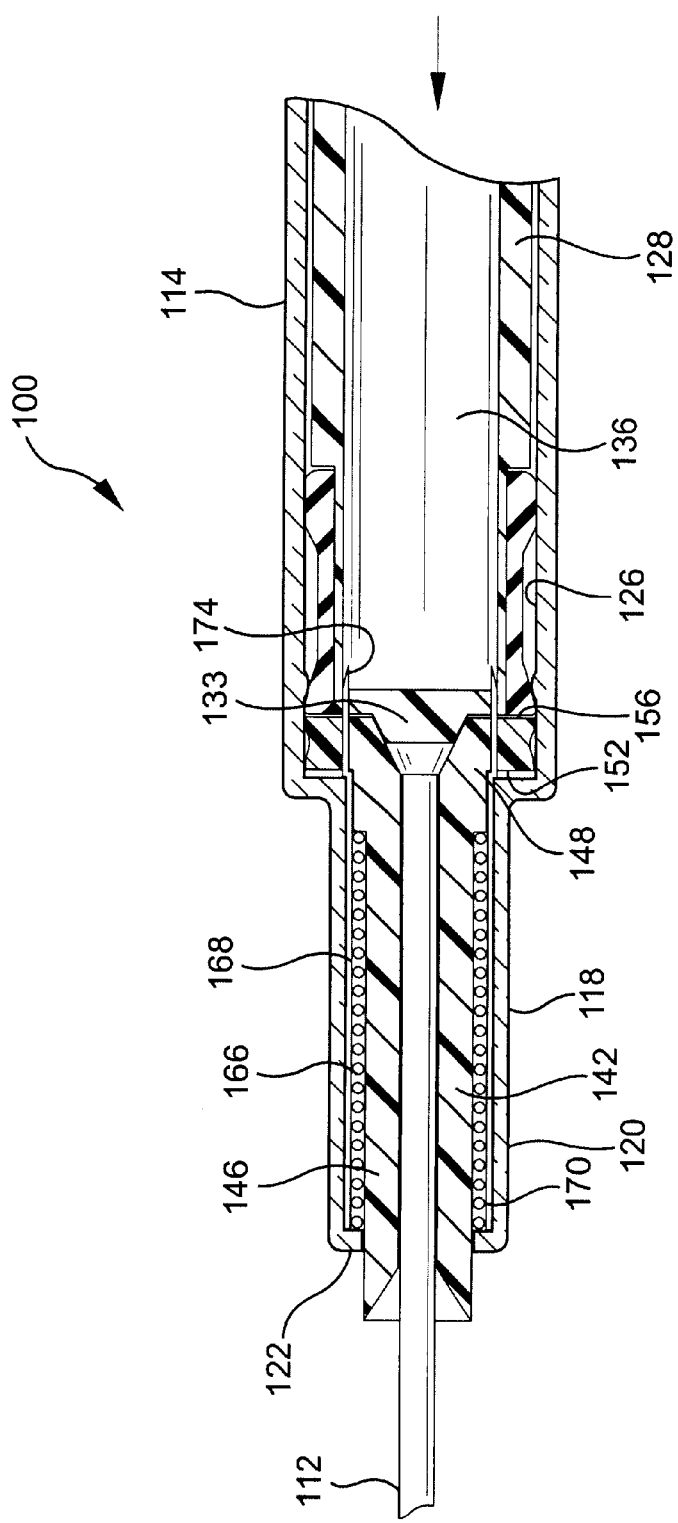
FIG. 12 is a cross-sectional view of another alternative embodiment of the invention illustrating the plunger moved distally to activate the needle retracting sequence.
Figure 13:
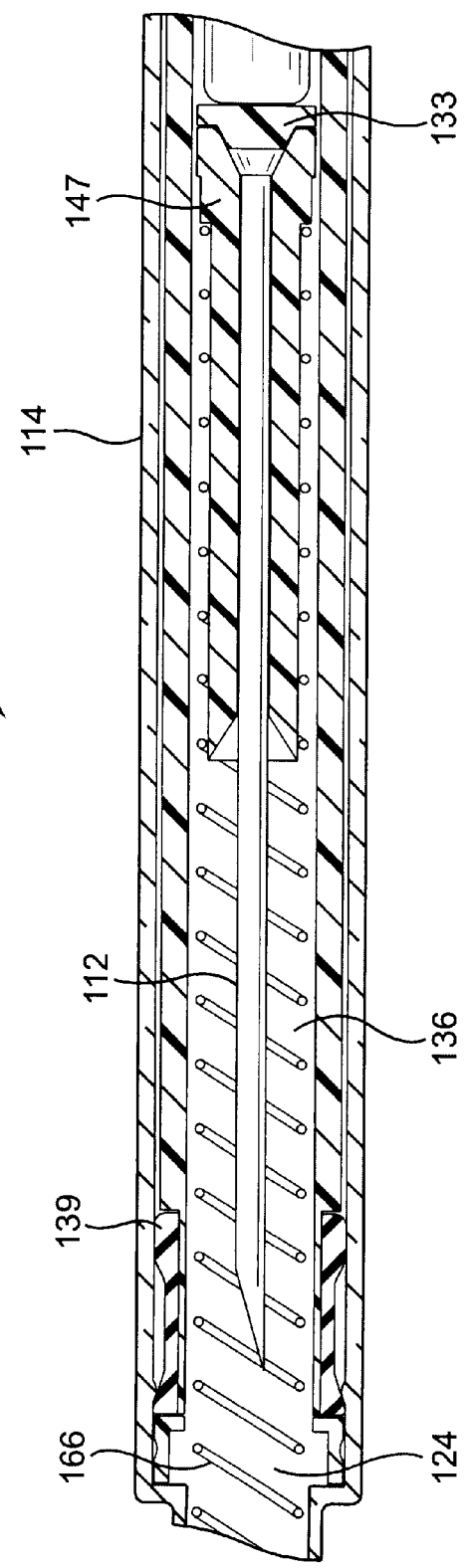
FIG. 13 is a cross-sectional view of the syringe of FIG. 12 illustrating the syringe after the needle retraction sequence is completed.
Figure 14:
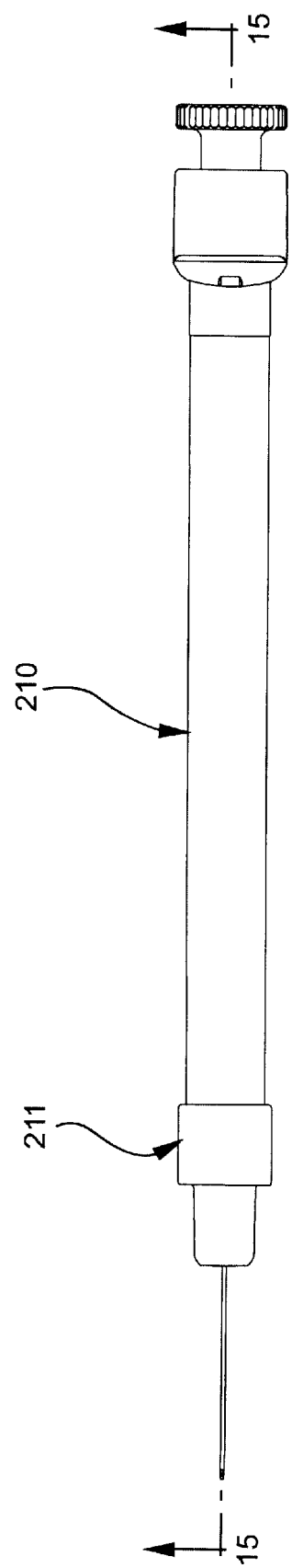
FIG. 14 is a side elevation view of the retracting needle assembly of the present invention with a syringe assembly.
Figure 15:
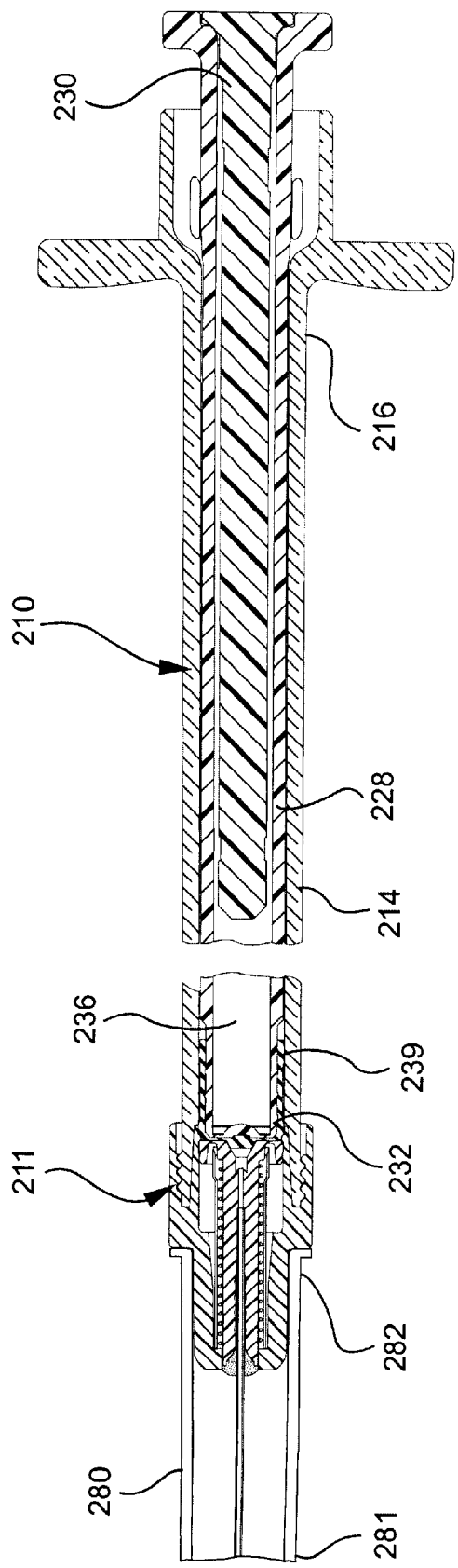
FIG. 15 is a cross-sectional view of the retracting needle assembly and syringe of FIG. 14 taken along line 15—15.
Figure 16:
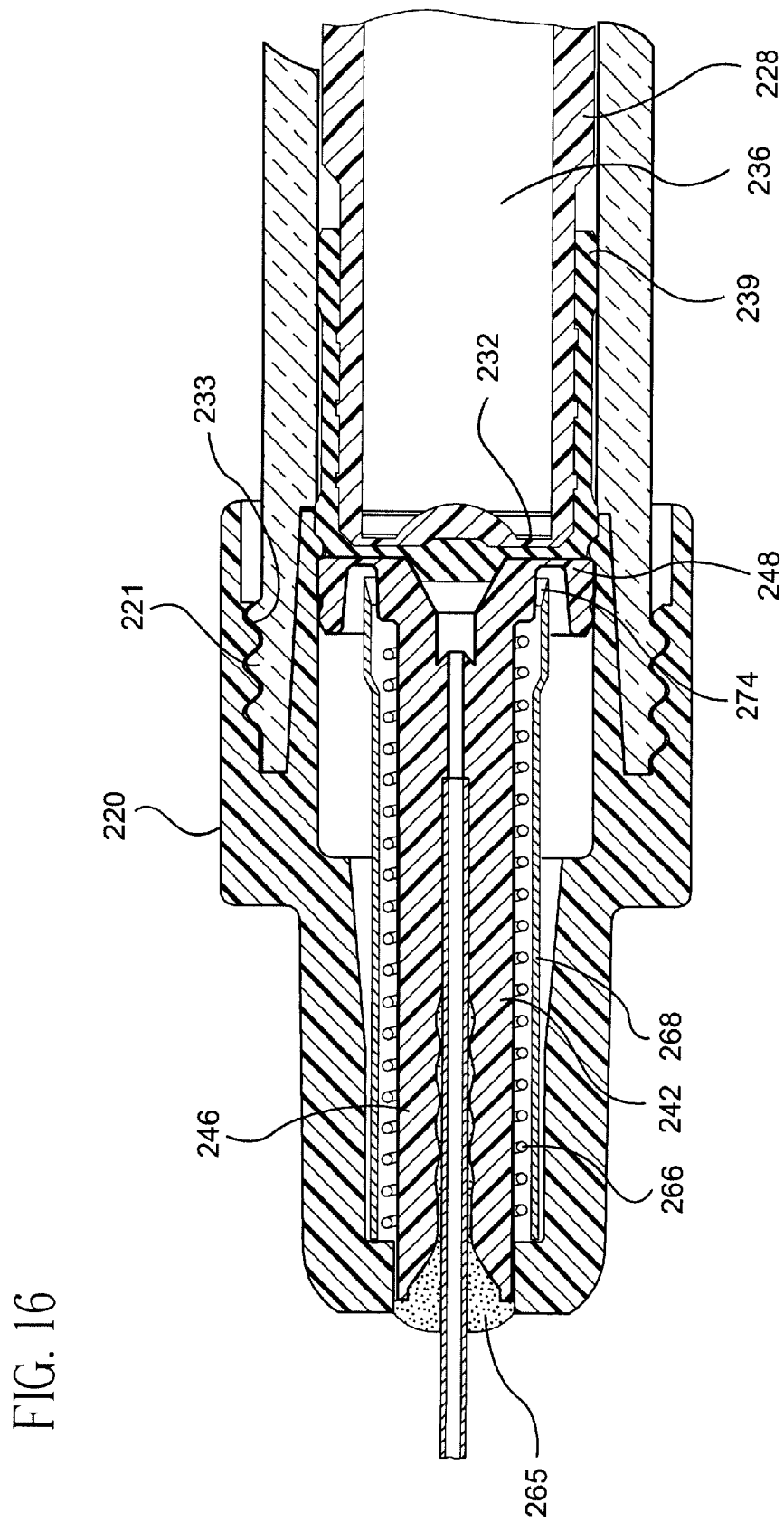
FIG. 16 is an enlarged cross-sectional view of the retracting needle assembly connected to a syringe assembly.
Figure 17:
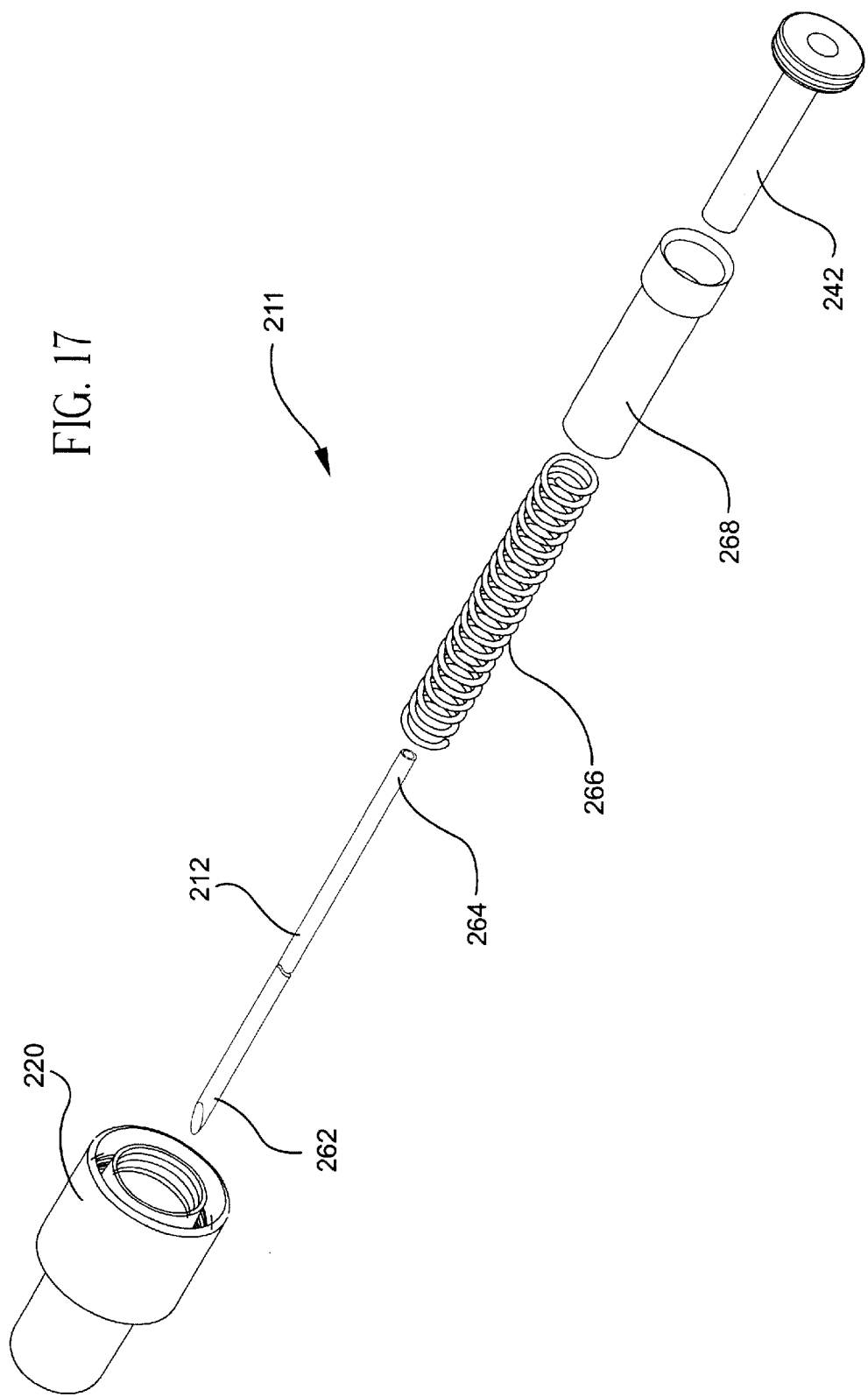
FIG. 17 is an exploded view of the retracting needle assembly.
Figure 18:
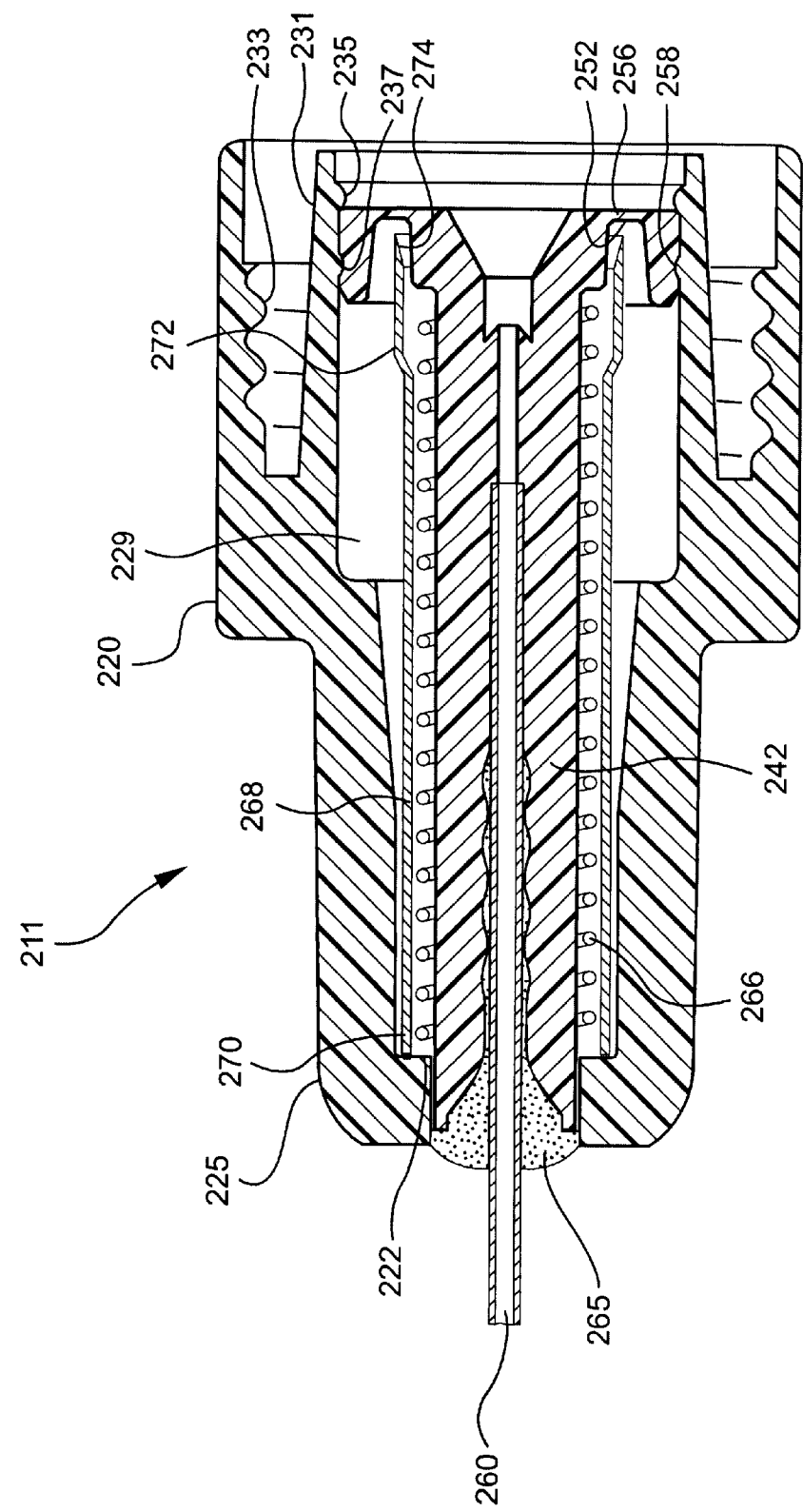
FIG. 18 is an enlarged cross-sectional view of the retracting needle assembly.
Figure 19:
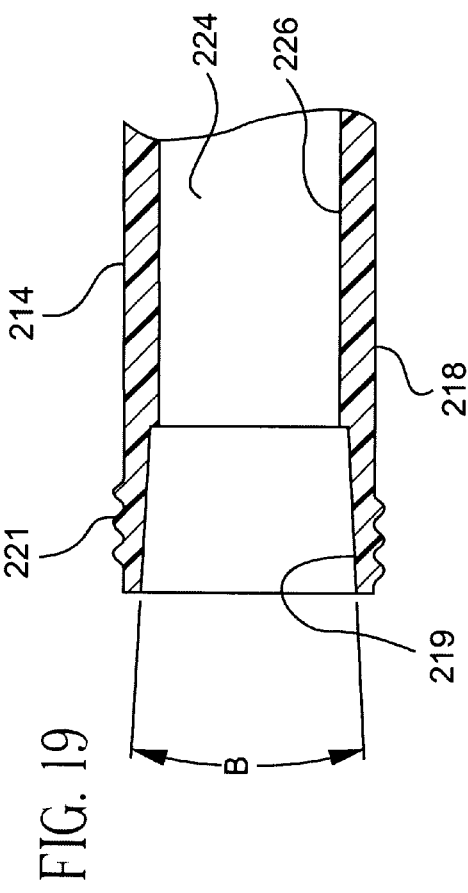
FIG. 19 is an enlarged cross-sectional view of the distal end of the syringe barrel of the syringe assembly.
Figure 20:
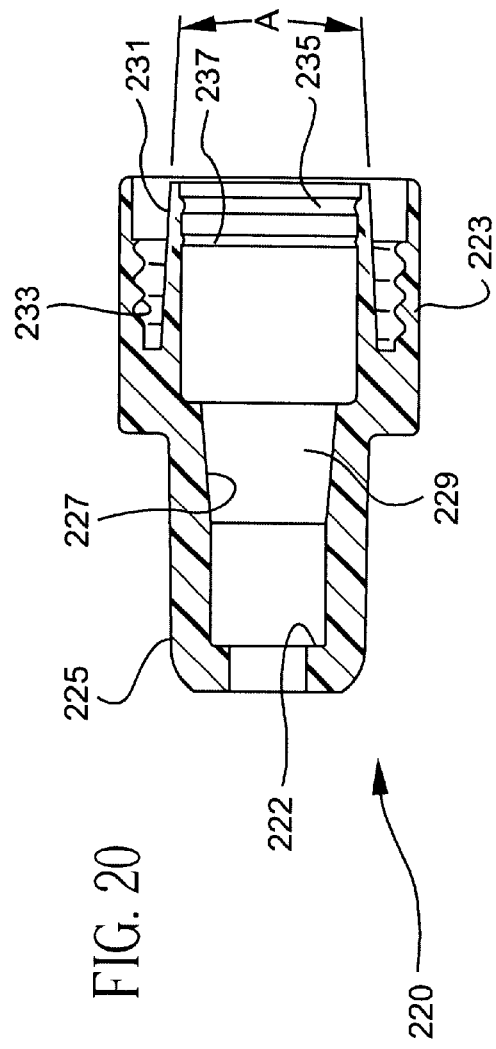
FIG. 20 is an enlarged cross-sectional view of the outer hub of the retracting needle assembly.
Figure 21:
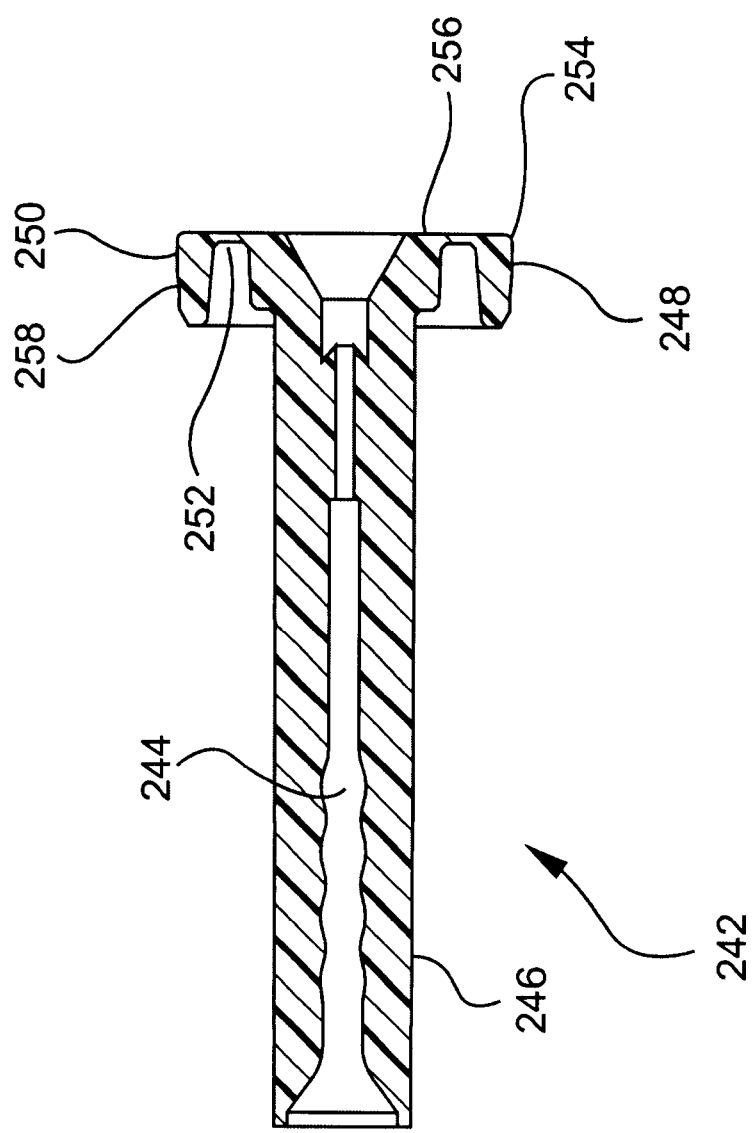
FIG. 21 is an enlarged cross-sectional view of the inner hub of the retracting needle assembly.

FIGS. 12–13 illustrate another alternative embodiment of the syringe of the present invention. The structure and function of this embodiment is substantially similar to that of the embodiment of FIGS. 1–7a except that upon activation of the needle retraction sequence, the hollow sleeve may remain in its position in the receiver of the barrel, or it may, as in the embodiment of FIGS. 1–7a, move to the cavity in the plunger.

A syringe 100 with a selectively retractable needle 112 includes an elongate barrel 114 having an open proximal end and a distal end 118 defining a receiver 120 with an inwardly projecting shoulder 122. Barrel 114 has a hollow bore 124 therethrough with an inside surface 126. Syringe 100 has a hollow plunger 128 with a closed distal end defining a cavity 136 within the plunger, and a resilient sealing member 139 at the distal end of the plunger. Syringe 100 also has an elongate hub 142 having a passageway therethrough and a distally extending stem 146 and a proximal flange 148. Flange 148 includes a distal surface 152 and a proximal surface 156. Needle 12 is mounted in the passageway of the hub so that the distal end of the needle projects distally outwardly and a fluid path in the needle is in fluid communication with the chamber of the barrel. An elongate spring 166 is disposed around stem 146 of hub 142 and is compressed between the receiver and the hub to provide a biasing force. A hollow sleeve 168 is sized to fit within receiver 120 over spring 166. Sleeve 168 has a distal end 170 and a proximal end with a sharp cutting edge 174.

When the user applies sufficient force, as illustrated in FIG. 12, a force greater than necessary to expel fluid from the barrel chamber, to plunger 128, hub 142 is sufficiently moved distally in receiver 120 for cutting edge 174 of sleeve 168 to cut through flange 148 and closed distal end 132 of the plunger to expose cavity 136 in the plunger. When cavity 136 in the plunger is exposed, the biasing force of spring 166 urges a sufficient movement of a cut portion 147 of the hub having needle 112 mounted therein, and a cut portion 133 of distal end 132 of the plunger into cavity 136 in the plunger to a position, illustrated in FIG. 13, wherein an inadvertent exposure of the needle is substantially prevented. Upon cutting through the flange and the closed distal end of the plunger there will be a frictional force between the inside of sleeve 168 and the cut portion 133 of the plunger and cut portion 147 of the hub which are inside the sleeve. There will also be a frictional force between the outside of the sleeve and the remaining portions of the hub and the plunger. If the frictional force between the outside sleeve 168 and the remaining portions of the hub and the plunger is greater than the frictional force between the inside of the sleeve and the cut portion of the hub and the cut portion of the closed distal end of the plunger, the sleeve will remain in its fixed position in the barrel after activation. If the frictional force between the inside of the sleeve and the cut portions of the hub and the distal end of the plunger which are in the sleeve is greater than the frictional forces between the outside of the sleeve and the remaining portions of the hub and the plunger, the cutter will travel into the cavity of the plunger along with the cut portions of the hub and the distal portion of the plunger. Accordingly, the structure does not have to rely totally on the spring always being able to provide enough force to dislodge the cut portions of the hub and the distal end of the plunger from the sleeve.

It should be noted that hub 142 does not include a groove in distal surface 152. The groove as illustrated in the embodiment of FIGS. 1–7a is helpful to assure lower cutting forces by reducing the thickness of the hub in the area where the sleeve will cut through the hub. However, the flange may be of uniform thickness or may have recesses or removed material on its proximal surface 156. In the alternative, the material of the flange of the hub can be a softer material than the stem to facilitate efficient cutting. The groove is just representative of the many possibilities, all of which are within the purview of the present invention.

FIGS. 14–21 illustrate another alternative embodiment of the present invention. The function of this embodiment is similar to that of the embodiment of FIGS. 12 and 13 except that this embodiment includes a separate needle assembly which can be attached to and removed from the distal end of a syringe barrel. An operable retracting needle assembly 211 includes an outer hub 220, an inner hub 242, a needle 212, an elongate spring 266 and a hollow sleeve 268. Needle assembly 211 is intended for use with a syringe barrel assembly 210 including a syringe barrel 214 having an inside surface 226 defining a chamber 224, an open proximal end 216, an open distal end 218 including a needle assembly engaging structure such as thread 221 and a distally-facing annular sealing surface 219. The syringe barrel assembly further includes a hollow elongate plunger 228 having a proximal end 230 and a closed distal end 232 defining a cavity 236 therein. The distal end of the plunger forms a slidable seal with the inside surface of the barrel. For example, the slidable seal may be formed by use of a resilient sealing member 239.

Outer hub 220 includes a proximal end 223, a distal end 225, an inside surface 227 defining a conduit 229 therethrough. The outer hub also includes a proximally-facing annular sealing surface 231 and an inwardly directed shoulder 222 in the conduit. The outer hub includes means for connecting the outer hub to the needle assembly engaging structure of syringe barrel 214 so that proximally facing annular sealing surface 231 contacts distally-facing annular sealing surface 219 of the syringe barrel. In this embodiment, means for connecting the outer hub to the syringe barrel includes thread 233 which is engageable with thread 221 of the syringe barrel.

Inner hub 242 includes a passageway 244 therethrough, a distally extending stem 246 and a proximal flange 248. The proximal flange includes an engagement 250 for engaging the barrel, a distal surface 252 and a proximal surface 256. An elongate needle 212 having a fluid path 260 therethrough includes a sharp distal end 262 and a proximal end 264. Needle 212 is mounted in passageway 244 of the inner hub so that sharp distal end 262 projects distally outwardly and fluid path 260 will be in fluid communication with the chamber of the syringe barrel when the needle assembly of the present invention is attached to the syringe barrel. There are numerous ways to mount a needle to a hub and in this embodiment adhesive 265 is used to secure the needle to the hub.

An elongate spring 266 is disposed about the stem of the inner hub. The spring is deflected to provide a bias between proximal flange 248 and inwardly directed shoulder 222 of the outer hub. In this embodiment spring 266 is a coil spring compressed between the flange and the inwardly directed shoulder to provide the bias. A hollow sleeve 268 is sized to fit within the conduit of the outer hub over the spring. The sleeve includes a distal end 270 disposed at inwardly-directed shoulder 222 and a proximal end 272 having a sharp edge 274 facing distal surface 252 of the flange. The needle and inner hub are preferably formed of stainless steel and plastic respectively. However, they can be integrally formed of thermoplastic material. The spring is desirably formed of a metallic material and preferably steel or stainless steel.

When needle assembly 211 of the present embodiment is attached to syringe barrel assembly 210 and a force greater than necessary to expel fluid from chamber 240 is applied to plunger 228, inner hub 242 is sufficiently moved distally in conduit 229 of the outer hub for a sharp edge 274 of sleeve 270 to cut through flange 248 of the inner hub and closed distal end 232 of the plunger to expose cavity 236 in the plunger. When the cavity 236 in the plunger is exposed, the bias of spring 266 urges a sufficient movement of a cut portion of the hub having a needle mounted therein and a cut portion of the distal end of the plunger into the cavity of the plunger wherein an inadvertent exposure to the sharp distal point of the needle is substantially prevented. As explained hereinabove, the hollow sleeve may or may not move into the cavity of the plunger after the proximal flange and the distal end of the plunger are cut.

Needle assembly 211 may further include an elongate hollow needle shield 280 having a distal end 281 and an open proximal end 282 removably engaged to outer hub 220.

As taught hereinabove, there are numerous ways to releasably connect the flange of the inner hub to the outer hub for holding the spring in a compressed state. These many ways include protuberances and/or recesses on either the flange or the outer hub to interact with each other. In this embodiment, protuberance 235 on the inside surface of the outer hub interacts with proximal edge 254 on the flange to keep the inner hub from moving in a proximal direction with respect to the outer hub. In addition, protuberance 237 on the inside surface of the outer hub interacts with depression or recess 258 on the flange of the inner hub to resist motion of the inner hub with respect to the outer hub in both the proximal and distal directions. There are numerous ways to connect the inner and outer hub and the snap fit arrangement taught herein is merely representative of all these methods which are within the purview of the present invention. In particular, adhesives, separate metal locking clips, ultrasonic welding, crimping, internally molded locking structure and the like can be used for releasably engaging the inner hub and the outer hub together.

In this embodiment, proximally-facing annular sealing surface 231 is a frusto-conically shaped surface positioned and dimensioned for mating with the complementary distally-facing frusto-conically shaped surface 219 on the syringe barrel. Angle A of frusto-conically shaped surface 231 on the outer hub is preferably substantially similar to Angle B of the frusto-conically shaped surface 219 on the barrel. The total included angle on frusto-conically shaped surface 231 is desirably between 3° and 178°. The total included Angle A is preferably between 3° and 9° with 6° being most preferred.

In this embodiment, means for connecting the outer hub to the needle assembly engaging structure of the syringe barrel includes at least one inwardly-facing thread on the outer hub and at least one outwardly-facing thread on the syringe barrel. This arrangement is merely representative of the many possibilities within the purview of the present invention. The threads may be outwardly facing on the needle assembly and inwardly facing on the barrel. Threads may be right-handed or left-handed and include single or multiple threads. It is also within the scope of the invention to have means for connecting the hub to the syringe barrel to include thread engaging structure such as at least one thread-engaging projection on either the outer hub or the barrel and a complementary thread on the other of the outer hub and the barrel. Threadable engagement using right-hand threads is preferred. A bayonet-type connection may also be used.

Figure 22:
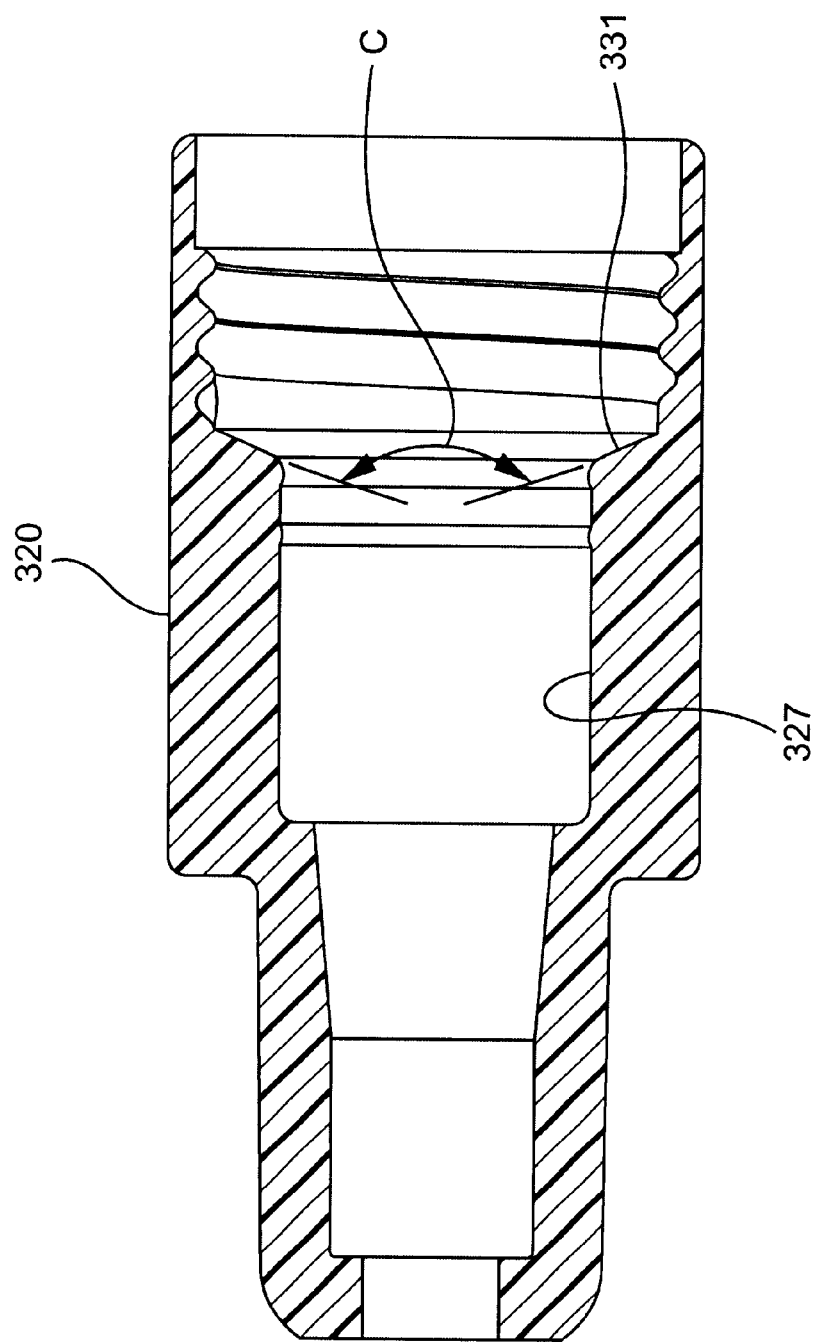
FIG. 22 is an enlarged cross-sectional view of an alternative outer hub of the retracting needle assembly.
Figure 23:
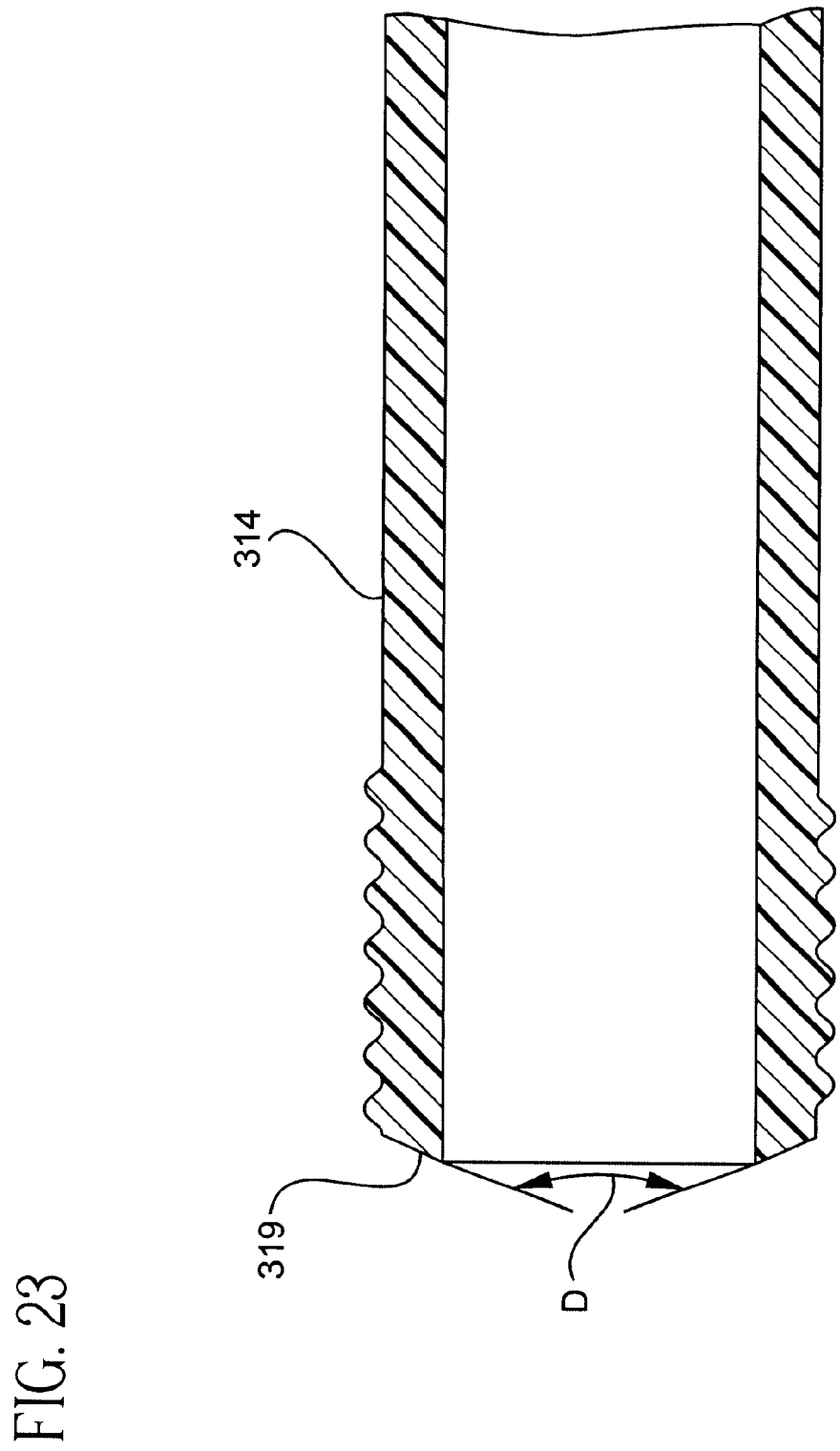
FIG. 23 is an enlarged cross-sectional view of the distal end of a syringe barrel for use with a retracting needle assembly having the outer hub of FIG. 22.

FIGS. 22 and 23 illustrate an alternative embodiment of the present needle assembly and is substantially similar in structure and function to the embodiment of FIGS. 14–21. In this embodiment, outer hub 320 includes a frusto-conically shaped proximally-facing annular sealing surface 331 formed on inner surface 327. It will mate with distally-facing annular sealing surface 319 of syringe barrel 314 which is also a frusto-conically shaped surface. The angle C of frusto-conically shaped surface on the outer hub is about between 90° and 150°. It is also preferred that Angle D of the frusto-conically shaped surface on the barrel be similar.

Figure 24:
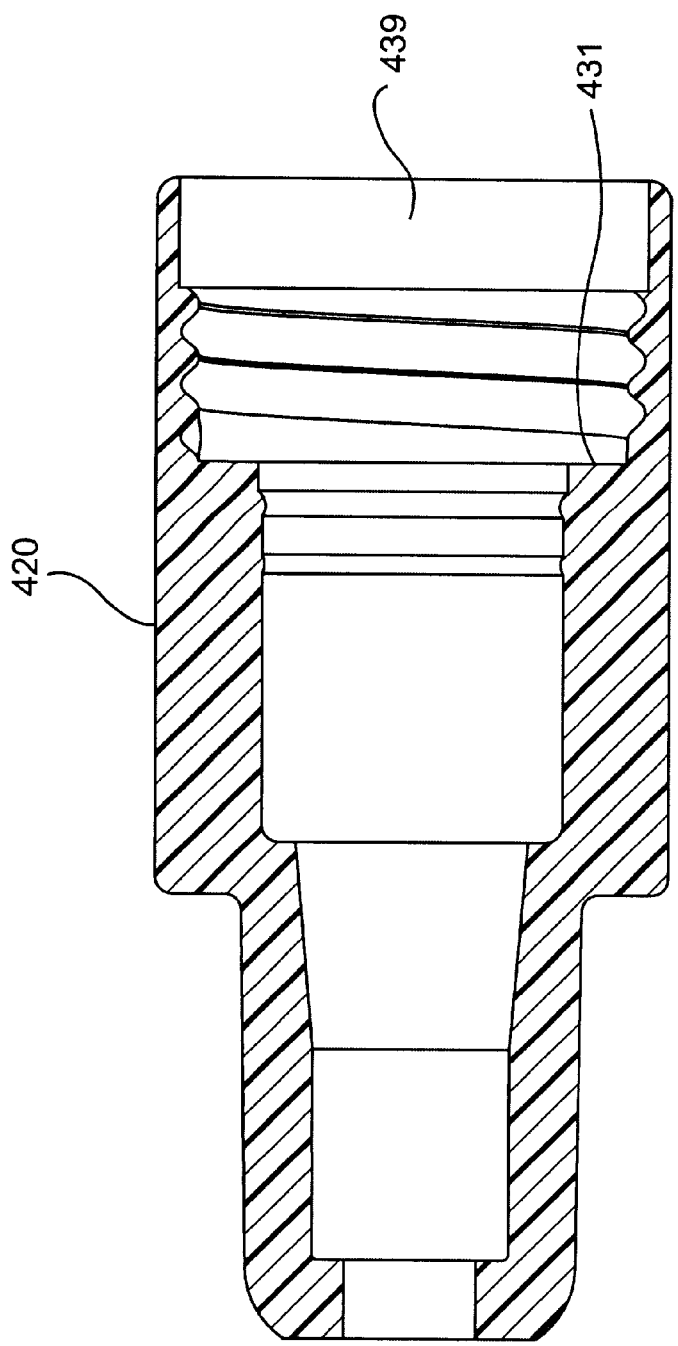
FIG. 24 is an enlarged cross-sectional view of another alternative outer hub of the retracting needle assembly.
Figure 25:
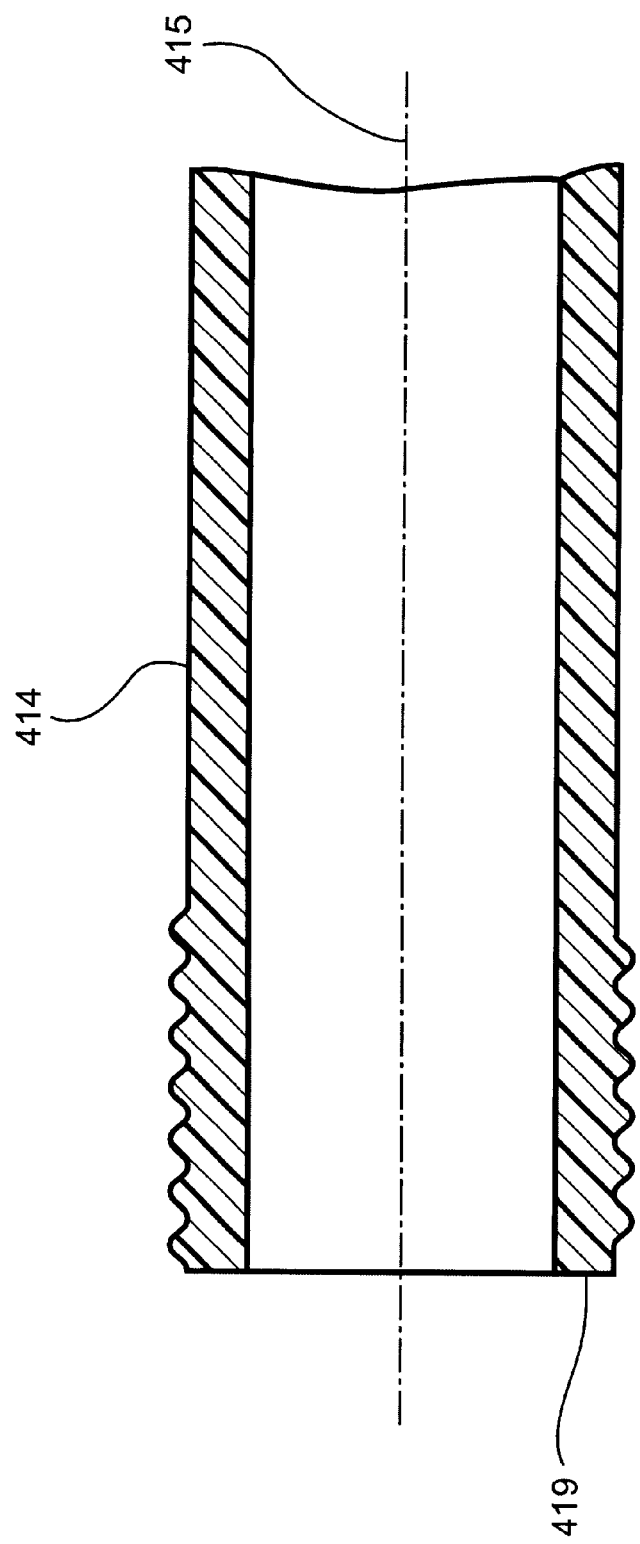
FIG. 25 is an enlarged cross-sectional view of the distal end of a syringe barrel for use with a retracting needle assembly having the outer hub of FIG. 24.

FIGS. 24 and 25 show another alternative embodiment of the needle assembly of the present invention. In this embodiment, outer hub 420 includes a proximally-facing annular sealing surface which is substantially flat and in a plane which is substantially perpendicular to longitudinal axis 439 of the outer hub. Syringe barrel 414 contains a distally-facing annular sealing surface 419 which is preferably substantially flat and in a plane substantially perpendicular to longitudinal axis 415 of the barrel. In all other regards this embodiment is substantially similar to the embodiment of FIGS. 14–21.

What is claimed is:

1. An operable retracting needle assembly for use with a syringe barrel assembly including a syringe barrel having an inside surface defining a chamber, an open proximal end, an open distal end including a needle assembly engaging structure and a distally facing annular sealing surface, and a hollow elongate plunger having a proximal end and a closed distal end defining a cavity therein, said distal end of said plunger forming a slidable seal with said inside surface of said barrel, comprising:

an outer hub having a proximal end, a distal end, an inside surface defining a conduit therethrough, a proximally facing annular sealing surface and an inwardly directed shoulder in said conduit, said outer hub including means for connecting said outer hub to said needle assembly engaging structure of said syringe barrel so that said proximally facing annular sealing surface contacts said distally facing annular sealing surface of said syringe barrel;

an inner hub having a passageway therethrough, said inner hub having a distally extending stem, a proximal flange with an engagement for releasably engaging said conduit of said outer hub, said stem being disposed within and sized for slidable movement within said cavity of said outer hub, said flange having a distal surface and a proximal surface;

a needle having a sharp distal end, a proximal end and a passageway therethrough, said proximal end of said needle being mounted in said passageway of said inner hub so that said sharp distal end projects distally outwardly;

an elongate spring disposed about said stem of said inner hub, said spring being deflected to provide a bias between said flange and said inwardly projecting shoulder; and a hollow sleeve sized to fit within said conduit of said outer hub over said spring, said sleeve having a distal end disposed at said shoulder and a proximal end having a sharp edge facing said distal surface of said flange so that when said needle assembly is installed on said syringe assembly and a distally directed force, greater than the force required to expel fluid from said chamber, is applied to said plunger, said inner hub is moved sufficiently distally in said outer hub for said sharp edge of said sleeve to cut through said flange and said closed distal end of said plunger to expose said cavity therein, thereby allowing said bias of said spring to urge a sufficient proximal movement of a cut portion of said hub having said needle mounted therein and a cut portion of said distal end of said plunger into said cavity in said plunger to a position wherein an inadvertent exposure of said sharp distal point is substantially prevented.

2. The needle assembly of claim 1 further including an elongate hollow needle shield having a distal end and an open proximal end removably engaged to said outer hub so that said needle shield covers said needle.

3. The needle assembly of claim 1 wherein said means for connecting said outer hub to said syringe barrel includes at least one thread on said outer hub.

4. The needle assembly of claim 3 wherein said at least one thread is a right-hand thread.

5. The needle assembly of claim 3 wherein said at least one thread is a multiple lead thread.

6. The needle assembly of claim 1 wherein said means for connecting said outer hub to said syringe barrel includes at least one thread engaging projection on said outer hub.

7. The needle assembly of claim 1 wherein said proximally facing annular sealing surface is a frusto-conically shaped surface having a total included angle of 3° to 178°.

8. The needle assembly of claim 7 wherein said frusto-conically shaped surface has a total included angle of 3° to 9°.

9. The needle assembly of claim 7 wherein said frusto-conically shaped surface has a total included angle of 6°.

10. The needle assembly of claim 1 wherein said inside surface of said conduit of said outer hub has one of a depression therein and a protuberance thereon, and wherein said flange on said inner hub has a conjugate to one of said depression and said protuberance, so that when said stem is disposed in said conduit with said spring compressed between said flange and said shoulder, said conjugates are engaged thereby retaining said inner hub in said outer hub.

11. The needle assembly of claim 1 wherein said sleeve further comprises an outward step adjacent said proximal end, said step serving to accept said cut portion of said flange to allow advancement of said cutter into said distal end of said plunger thereby facilitating cutting through said distal end of said plunger to expose said cavity.

12. The needle assembly of claim 1 wherein said sleeve is formed from a metallic material.

13. The needle assembly of claim 12 wherein said metallic material is stainless steel.

14. The needle assembly of claim 12 wherein said proximal end of said sleeve is subjected to a secondary process to help produce said sharp edge.

15. The needle assembly of claim 14 wherein said process to help produce said sharp edge is selected from the group consisting of grinding, electrochemical processing, honing and combinations thereof.

16. The needle assembly of claim 1 wherein said inner hub and said needle are integrally formed of thermoplastic material.

17. The needle assembly of claim 1 wherein said spring is formed from a metallic material.

18. The needle assembly of claim 1 further comprising being sealed in a package formed from material substantially resistance to the passage of microorganisms and exposed to conditions that render any microorganisms therein substantially non-viable.

19. The needle assembly of claim 1 further including a syringe barrel having an inside surface defining a chamber, an open proximal end, an open distal end including a needle assembly engaging structure and a distally facing annular sealing surface, said hub being threadably engaged to said collar so that said annular sealing surface of said hub contacts said annular sealing surface of said barrel.

20. An operable retracting needle assembly for use with a syringe barrel assembly including a syringe barrel having an inside surface defining a chamber, an open proximal end, an open distal end including a thread and a distally facing frusto-conically shaped annular sealing surface, and a hollow elongate plunger having a proximal end and a closed distal end defining a cavity therein, said distal end of said plunger forming a slidable seal with said inside surface of said barrel, comprising:

an outer hub having a proximal end, a distal end and an inside surface defining a conduit therethrough, a proximally facing frusto-conically shaped annular sealing surface having a total included angle of 3° to 9° and an inwardly directed shoulder in said conduit, said outer hub including a thread engaging structure for connecting said outer hub to said thread on said syringe barrel so that said proximally facing annular sealing surface contacts said distally facing annular sealing surface of said syringe barrel;

an inner hub having a passageway therethrough, said inner hub having a distally extending stem, a proximal flange with an engagement for releasably engaging said conduit of said outer hub, said stem being disposed within and sized for slidable movement within said cavity of said outer hub, said flange having a distal surface and a proximal surface;

a needle having a sharp distal end, a proximal end and a passageway therethough, said proximal end of said needle being mounted in said passageway of said inner hub so that said sharp distal end projects distally outwardly;

an elongate spring disposed about said stem of said inner hub, said spring being deflected to provide a bias between said flange and said inwardly projecting shoulder; and a hollow sleeve sized to fit within said conduit of said outer hub over said spring, said sleeve having a distal end disposed at said shoulder and a proximal end having a sharp edge facing said distal surface of said flange so that when said needle assembly is installed on said syringe assembly and a distally directed force, greater than the force required to expel fluid from said chamber is applied to said plunger, said inner hub is moved sufficiently distally in said outer hub for said sharp edge of said sleeve to cut through said flange and said closed distal end of said plunger to expose said cavity therein, thereby allowing said bias of said spring to urge a sufficient proximal movement of a cut portion of said hub having said needle mounted therein and a cut portion of said distal end of said plunger into said cavity in said plunger to a position wherein an inadvertent exposure of said sharp distal point is substantially prevented.

21. The needle assembly of claim 20 further including an elongate hollow needle shield having a distal end and an open proximal end removably engaged to said outer hub so that said needle shield covers said needle.

22. The needle assembly of claim 20 wherein said thread engaging structure for connecting said outer hub to said syringe barrel includes at least one thread.

23. The needle assembly of claim 22 wherein said at least one thread is a multiple lead thread.

* * * * *